United States Patent
Husain et al.

(10) Patent No.: US 11,460,466 B2
(45) Date of Patent: Oct. 4, 2022

(54) RAPID TEST BREATHALYZER AND METHODS OF USE THEREOF

(71) Applicant: JLabs, Co., Arlington, VA (US)

(72) Inventors: Jamil Husain, Arlington, VA (US); Jeffrey Dawson, Arlington, VA (US); David White, Arlington, VA (US)

(73) Assignee: JLabs, Co., McLean, VA (US)

( * ) Notice: Subject to any disclaimer, the term of this patent is extended or adjusted under 35 U.S.C. 154(b) by 0 days.

(21) Appl. No.: 17/644,896

(22) Filed: Dec. 17, 2021

(65) Prior Publication Data

US 2022/0137033 A1      May 5, 2022

Related U.S. Application Data

(63) Continuation of application No. PCT/US2021/072078, filed on Oct. 28, 2021.
(Continued)

(51) Int. Cl.
*G01N 33/53* (2006.01)
*B01L 3/00* (2006.01)
(Continued)

(52) U.S. Cl.
CPC ........... *G01N 33/5302* (2013.01); *A61B 5/05* (2013.01); *A61B 5/095* (2013.01); *A61B 5/097* (2013.01); *B01L 3/502715* (2013.01); *G01N 1/22* (2013.01); *G01N 33/497* (2013.01); *G01N 33/54346* (2013.01); *G01N 33/54388* (2021.08);
(Continued)

(58) Field of Classification Search
CPC ............... G01N 33/5302; G01N 33/53; G01N 33/54388; G01N 33/54346; G01N 1/22; G01N 2201/2244; G01N 2033/4975; A61B 5/05; A61B 5/095; A61B 5/097; B01L 3/502715; B01L 3/5027; B01L 3/502;
(Continued)

(56) References Cited

U.S. PATENT DOCUMENTS

| 2015/0295562 A1* | 10/2015 | Agarwal | G01N 33/0047 73/23.3 |
|---|---|---|---|
| 2016/0109440 A1 | 4/2016 | Sherwood | |
| 2020/0200733 A1 | 6/2020 | Nolan et al. | |

FOREIGN PATENT DOCUMENTS

| WO | 2020/123565 A1 | 6/2020 |
| WO | 2020/186335 A1 | 9/2020 |

OTHER PUBLICATIONS

Kumud Malika Tripathi et al: "Recent advances in engineered graphene and composites for detection of volatile organic compounds (VOCs) and non-invasive diseases diagnosis", CARBON, vol. 110, Dec. 1, 2016 (Dec. 1, 2016), pp. 97-129, XP055448434, GB ISSN: 0008-6223, DOI: 10.1016/j.carbon.2016.08.040.
(Continued)

*Primary Examiner* — Christine T Mui
(74) *Attorney, Agent, or Firm* — Polsinelli PC

(57) ABSTRACT

Described herein are rapid breath testing devices, systems and methods. The device may include a mouthpiece operable to receive air flow from a breath; and a cassette comprising a biosensor and a cassette conduit, the cassette removably connected to the mouthpiece such that at least a sample of the air flow passes through the cassette conduit and over the biosensor. The biosensor may include a plurality of graphene-based sensors and may be operable to detect at least one volatile organic compound in the air flow sample.

29 Claims, 16 Drawing Sheets

Related U.S. Application Data

(60) Provisional application No. 63/165,524, filed on Mar. 24, 2021, provisional application No. 63/107,296, filed on Oct. 29, 2020.

(51) Int. Cl.
  *G01N 1/22* (2006.01)
  *A61B 5/05* (2021.01)
  *A61B 5/095* (2006.01)
  *G01N 33/543* (2006.01)
  *G01N 33/497* (2006.01)
  *A61B 5/097* (2006.01)
  *B82Y 40/00* (2011.01)
  *B82Y 5/00* (2011.01)

(52) U.S. Cl.
  CPC ..... *B01L 2200/027* (2013.01); *B01L 2200/04* (2013.01); *B01L 2200/10* (2013.01); *B01L 2300/0645* (2013.01); *B82Y 5/00* (2013.01); *B82Y 40/00* (2013.01); *G01N 2001/2244* (2013.01); *G01N 2033/4975* (2013.01); *G01N 2800/56* (2013.01)

(58) Field of Classification Search
  CPC .. B01L 3/50; B01L 2200/027; B01L 2200/04; B01L 2200/10
  USPC .......................................................... 73/23.3
  See application file for complete search history.

(56) References Cited

OTHER PUBLICATIONS

International Search Report dated Feb. 16, 2022, Application # PCT/US2021/072078.

* cited by examiner

US 11,460,466 B2

RAPID TEST BREATHALYZER AND METHODS OF USE THEREOF

CROSS-REFERENCE TO RELATED APPLICATIONS

This application is a continuation of PCT Application No. PCT/US21/72078, filed Oct. 28, 2021, which claims priority to U.S. Provisional Application No. 63/107,296, filed Oct. 29, 2020, and U.S. Provisional Application No. 63/165,524, filed Mar. 24, 2021, the contents of which are entirely incorporated by reference herein.

FIELD

The present disclosure relates to a devices, systems, and methods for real-time detection of volatile organic compounds in breath samples.

BACKGROUND

There are a variety of biomarkers present in human breath which indicate a range of disease states. While breath can consist of endogenous and exogenous volatile organic compounds (VOCs), the endogenous VOCs can contain relevant indicators of disease. These VOCs can serve as a rapid noninvasive diagnostic to enhance early detection of a variety of diseases including but not limited to cancer, asthma, COPD, kidney dysfunction, and respiratory illness.

One of the principal limitations of existing breath detection technology is the relatively low concentrations of endogenous VOCs present in the breath. This drives collection of multiple breaths onto sorbent materials which inherently biases the signal. Another limitation is the complex mixture of VOCs present for disease states. Respiratory illnesses tend to have four to eight VOCs presents in different concentrations which would typically require 4-8 selective sensors with limited cross sensitivity to detect.

Some airborne pathogens are either so dangerous or so contagious, or both, that rapid detection systems and techniques are often critical in order to enable the continued operation of facilities or various activities without substantial harm and inconvenience to the public.

SUMMARY

Provided herein are embodiments of rapid breath testing devices, systems, and methods.

In accordance with an aspect of the disclosure, a rapid breath testing system includes a mouthpiece operable to receive air flow from a breath and a cassette comprising a biosensor and a cassette conduit having a cassette inlet and a cassette outlet. The mouthpiece is removably connected to the cassette inlet such that at least a sample of the air flow passes through the cassette conduit and over the biosensor. The biosensor comprises a plurality of graphene-based sensors and the biosensor is operable to detect a presence of at least one volatile organic compound (VOC) in the air flow sample through the graphene-based sensors. In some aspects, the system may further include a base that is operable to receive to the cassette in a removeable manner.

In accordance with another aspect of the disclosure, a rapid breath testing device comprises: a mouthpiece operable to receive air flow from a breath; a body comprising a conduit for directing the air flow through the device; and a cassette comprising a biosensor and a cassette conduit, the cassette removably connected to the conduit of the body such that at least a sample of the air flow passes through the cassette conduit and over the biosensor. The biosensor comprises graphene and is operable to detect at least one volatile organic compound in the air flow sample.

In accordance with an additional aspect of the disclosure, a mouthpiece includes: a body; a body conduit through the body of the mouthpiece, the body conduit comprising a breath inlet, an exhaust, and a sample air flow outlet; and a check valve within the body conduit. The mouthpiece is operable to receive air flow from a breath of a user at the breath inlet and pass at least a sample of the air flow out the sample air flow outlet, and the check valve is operable to prevent backflow of the air flow to the user.

In accordance with a further aspect of the disclosure, a cassette includes a biosensor comprising a plurality of graphene-based sensors and a cassette conduit having a cassette inlet and a cassette outlet. The biosensor is operable to detect a presence of at least one VOC in an air flow sample through the plurality of graphene-based sensors, and the air flow sample passes through the cassette conduit and over the biosensor and the cassette.

In an aspect, the disclosure further provides a biosensor comprising: a biosensor inlet configured to receive a sample of air flow from a breath; a plurality of subsets of graphene-based sensors of a plurality of graphene-based sensors that are each configured to: encounter corresponding portions of the air flow sample received at the biosensor inlet; and facilitate detection of a VOC in the air flow sample based on encounters of the corresponding portions of the air flow sample with each of the plurality of subsets of graphene-based sensors.

In another aspect, the disclosure provides a method for detecting at least one VOC in an air flow sample. The method includes: receiving an air flow from a breath passed into a breath inlet of a mouthpiece of a rapid breath testing system, the rapid breath testing system further comprising a cassette comprising a biosensor connected to the mouthpiece, wherein a sample of the air flow passes from a sample air flow outlet of the mouthpiece through a cassette conduit of the cassette; detecting, through a plurality of graphene-based sensors of the biosensor, at least one VOC in the air flow sample.

Other aspects and iterations of the invention are described more thoroughly below.

BRIEF DESCRIPTION OF THE DRAWINGS

The description will be more fully understood with reference to the following figures and data graphs, which are presented as various embodiments of the disclosure and should not be construed as a complete recitation of the scope of the disclosure. It is noted that, for purposes of illustrative clarity, certain elements in various drawings may not be drawn to scale. Understanding that these drawings depict only exemplary embodiments of the disclosure and are not therefore to be considered to be limiting of its scope, the principles herein are described and explained with additional specificity and detail through the use of the accompanying drawings in which.

DETAILED DESCRIPTION

Figure 1:
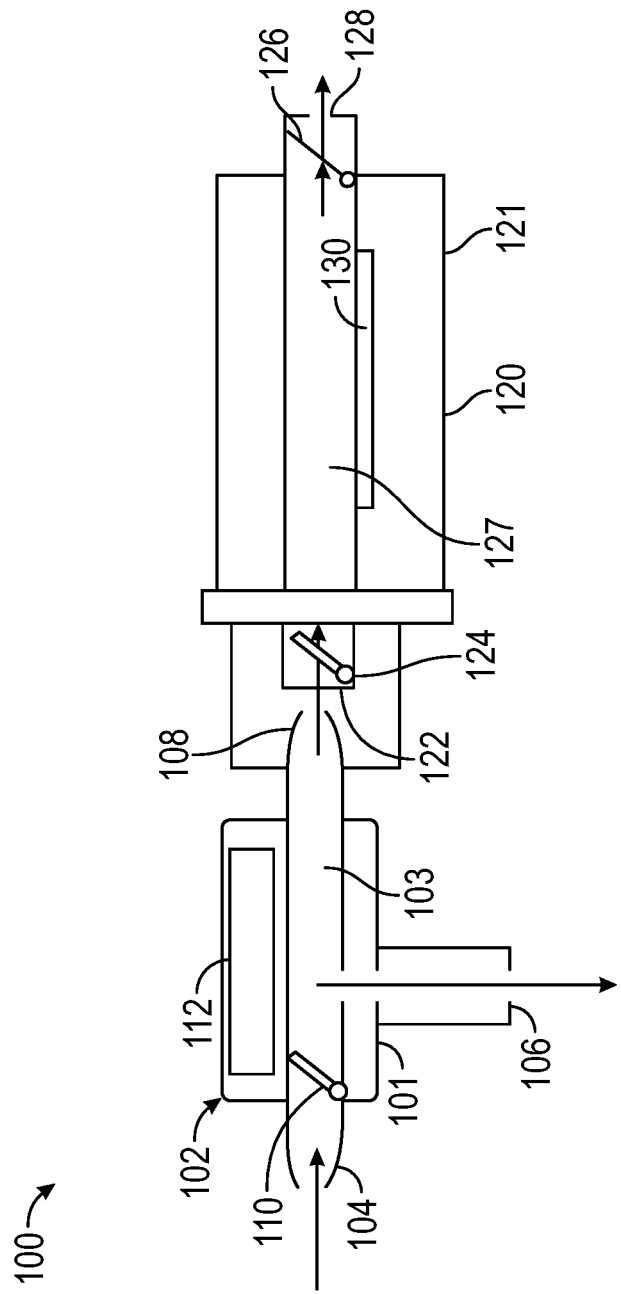
FIG. 1 is a rapid breath testing system in one example.

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure. Thus, the following description and drawings are illustrative and are not to be construed as limiting. Numerous specific details are described to provide a thorough under-standing of the disclosure. However, in certain instances, well-known or conventional de-tails are not described in order to avoid obscuring the description.

Reference to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments; and, such references mean at least one of the embodiments. Moreover, various features are described which may be exhibited by some embodiments and not by others.

As used herein, the terms "comprising," "having," and "including" are used in their open, non-limiting sense. The terms "a," "an," and "the" are understood to encompass the plural as well as the singular.

Moreover, claim language reciting "at least one of" a set indicates that one member of the set or multiple members of the set satisfy the claim. For example, claim language reciting "at least one of A and B" means A, B, or A and B.

Generally, the ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc. All ranges and values disclosed herein are inclusive and combinable. For examples, any value or point described herein that falls within a range described herein can serve as a minimum or maximum value to derive a sub-range, etc. Other than in the operating examples, or where otherwise indicated, all numbers expressing quantities of ingredients and/or reaction conditions may be modified in all instances by the term "about," meaning within +/−5% of the indicated number.

Reference to "rapid breath testing system", "rapid test breathalyzer" (RTB) and "rapid breath testing device", and "device" are used interchangeably to refer to a device, apparatus, and system operable to detect a VOC with a single breath.

The terms used in this specification generally have their ordinary meanings in the art, within the context of the disclosure, and in the specific context where each term is used. Alternative language and synonyms may be used for any one or more of the terms discussed herein, and no special significance should be placed upon whether or not a term is elaborated or discussed herein. In some cases, synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any example term. Likewise, the disclosure is not limited to various embodiments given in this specification.

Provided herein are devices, systems, and methods for real-time detection of volatile organic compounds (VOCs) in breath samples. In particular, provided herein is a rapid breath testing device. The rapid test breathalyzer (RTB) disclosed herein addresses the concerns with the existing breath detection technology. The VOCs may be a pathogen or may be a disease marker present in a user's breath. In some examples, the pathogen may be a virus or bacteria. In at least one example, the virus may be SARS-CoV-2. Non-limiting examples of diseases with VOCs detectable in the breath include cancer, asthma, COPD, kidney dysfunction, and respiratory illness.

Figure 2:
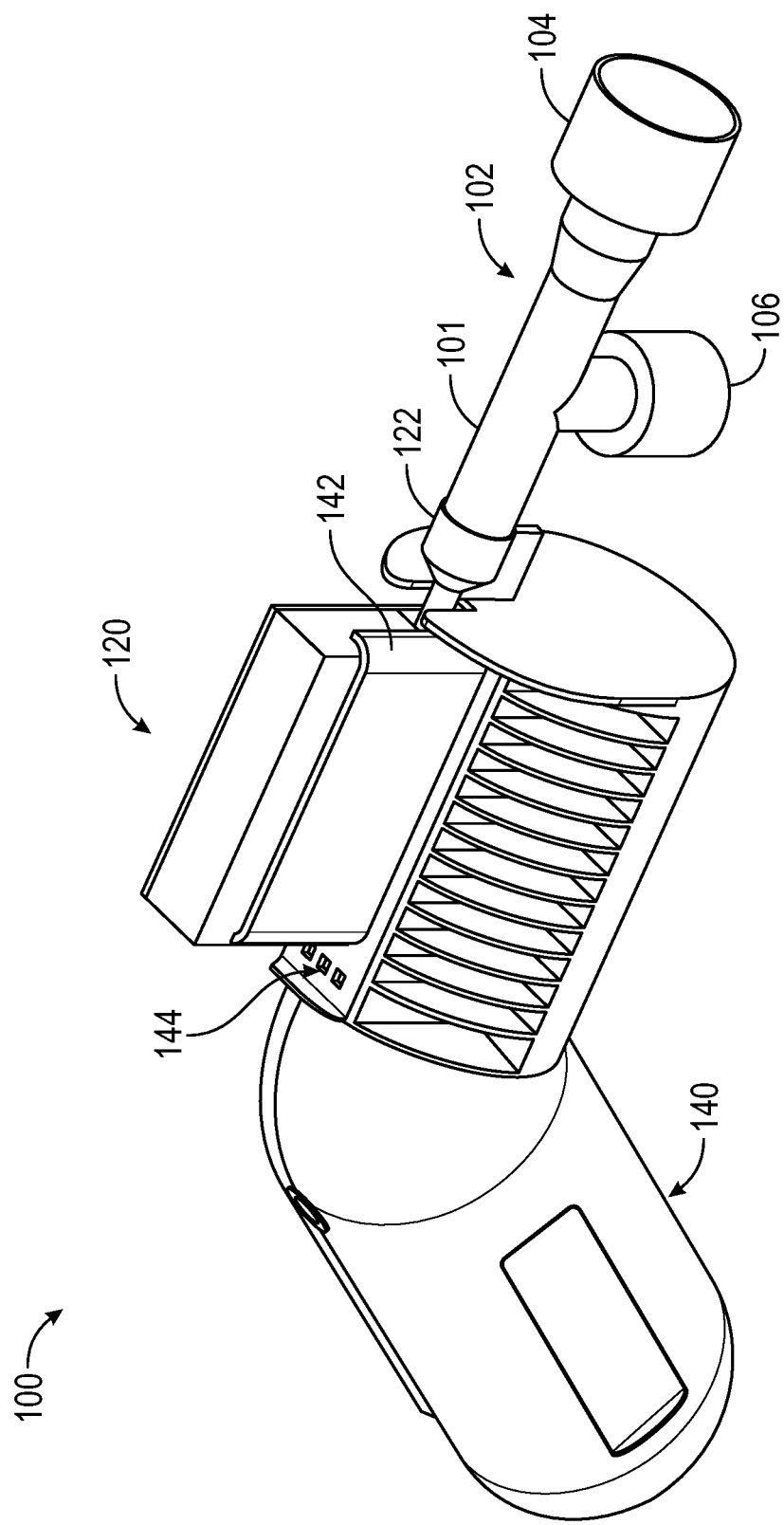
FIG. 2 is a rapid breath testing system in one example.

FIGS. 1 and 2 are an example rapid breath testing system (RTB device) 100 that includes a mouthpiece 102 operable to receive air flow from a breath, and a cassette 120 including a biosensor 130 and a cassette conduit 127 having a cassette inlet 122 and a cassette outlet 128. The biosensor 130 includes a plurality of graphene-based sensors and the biosensor 130 is operable to detect a presence of at least one volatile organic compound (VOC) in the air flow sample through the graphene-based sensors. Surprisingly, the use of a plurality of graphene-based sensors may allow for only a portion of a breath to be needed to detect a VOC in the breath. In various embodiments, the system 100 is operable to detect a VOC using only a single breath from a user. As seen in FIG. 2, the rapid breath testing system 100 may further include a base 140 operable to receive the cassette 120. The base 140 may be electronically connected to the biosensor 130 in the cassette 120.

Disposable Mouthpiece

Figure 3A:
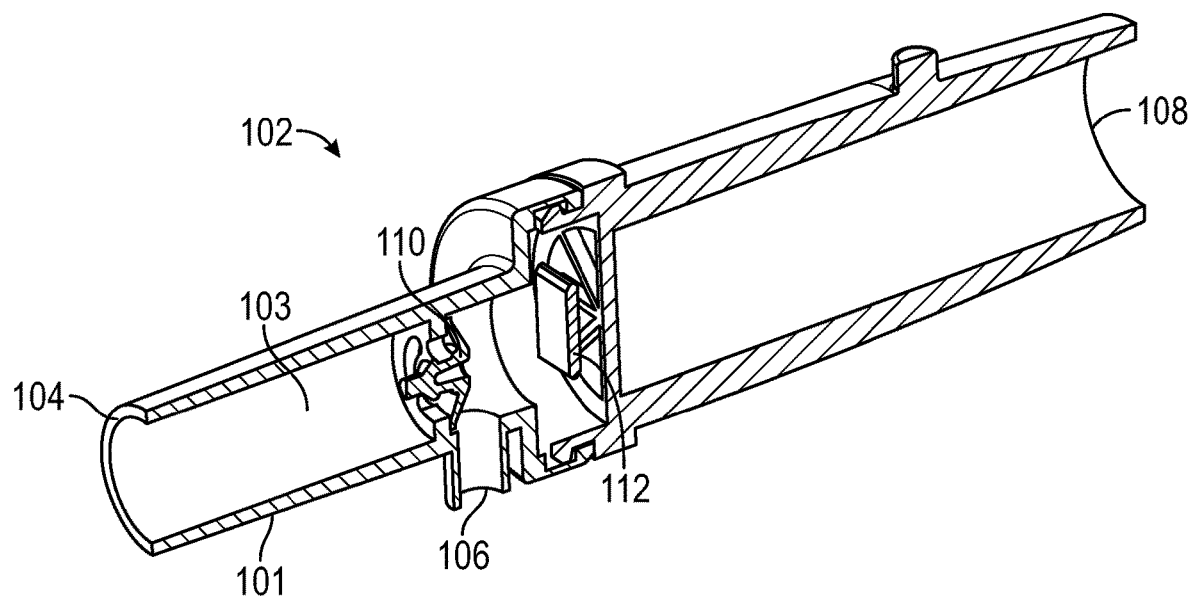
FIG. 3A is a mouthpiece with a desiccant in one example.
Figure 3B:
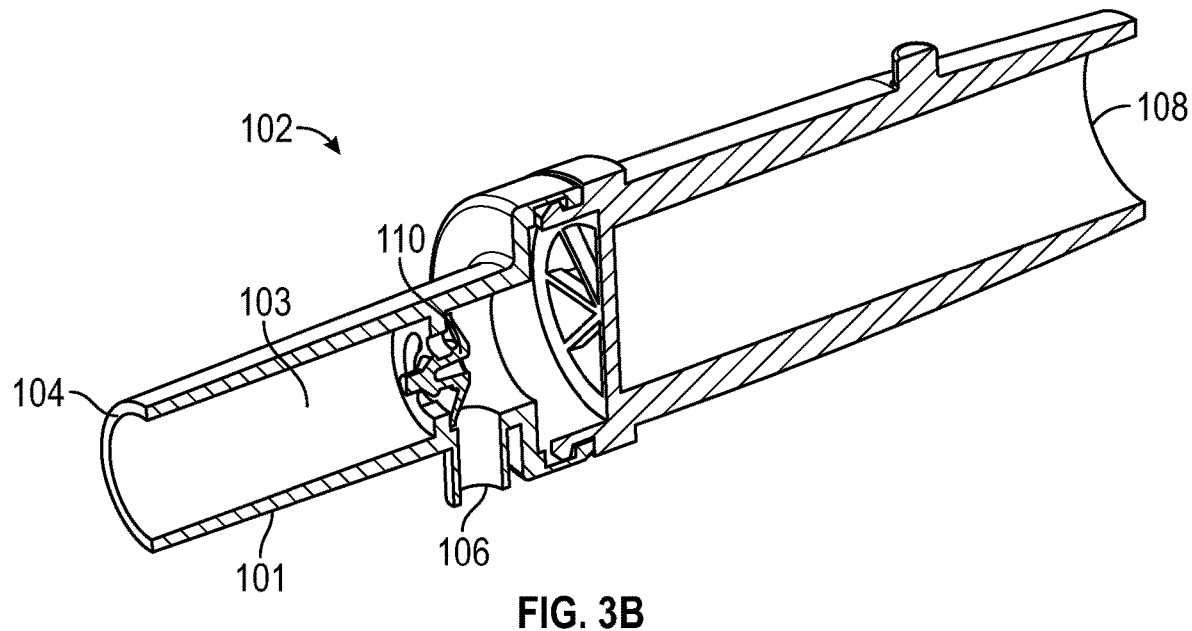
FIG. 3B is a mouthpiece made of a desiccant material in one example.

As the RTB device may be used by many users who carry potential infections, the RTB device may include a disposable mouthpiece. FIGS. 3A and 3B show an example mouthpiece 102 of the rapid breath testing system 100. Referring back to FIG. 1, in some embodiments, the mouthpiece 102 is removably connected to the cassette inlet 122 such that at least a sample of the air flow passes through the cassette conduit 127 and over the biosensor 130.

Referring again to FIGS. 3A and 3B, the mouthpiece 102 includes a body 101 having a body conduit 103 having a breath inlet 104, an exhaust 106, and a sample air flow outlet 108. The breath inlet 104 is operable to receive a breath from a user and the airflow of the breath may pass through the body conduit 103 such that a portion of the air flow exits the body conduit 103 through the exhaust 106 and a portion of the air flow exits the body conduit 103 through the sample air flow outlet 108. The mouthpiece 102 and/or the cassette 120 may have internal breath flow design which minimizes the volume directly over the biosensor. This may prolong the lifetime of the device and enable spatial separation of different parts of the breath which is inherently precluded in preconcentration schemes of other devices. This enables discrete analysis of different parts of the breath which enables better classification of data. In some embodiments, 80% to 99% of the air flow from the breath entering the breath inlet 104 exits through the exhaust 106 and any remaining air flow is the air flow sample. In at least one example, 95% to 99% of the air flow from the breath entering the breath inlet 104 exits through the exhaust 106 and any remaining air flow is the air flow sample that exits through the sample air flow outlet 108.

The sample air flow outlet 108 of the mouthpiece 102 is operable to removably connect to the cassette inlet 122, such that the mouthpiece 102 and the cassette 120 are fluidly connected. For example, the air flow sample exits the body conduit 103 of the mouthpiece 102 through the sample air flow outlet 108 and into the cassette inlet 122. The mouthpiece 102 and the cassette 120 may be press-fit together so that the mouthpiece 102 and the cassette 120 may be easily and quickly connected together. In some examples, the connection is airtight, such that no air flow is able to escape through the connection.

In some embodiments, the mouthpiece 102 may include one or more one-way valves 110 to limit cross contamination. For example, the mouthpiece 102 may include a passive check valve 110. The check valve 110 may be any check valve operable to limit flow in a single direction. In some example, the passive check valve 110 is an umbrella check valve, a duckbill valve, or a ball and spring check valve. In addition, the check valve may be tuned to open at a set pressure. In some aspects, this may further limit the airflow through the device.

In an embodiment, the mouthpiece 102 may further include a desiccant 112. The desiccant 112 may be operable to remove liquid from the air flow, such that the desiccant 112 reduces the humidity of the air flow sample as compared to the air flow from the breath. In other embodiments, the mouthpiece body 101 is made of the desiccant. In this embodiment, a desiccant is not also needed to be within the body conduit. Breath has a wide variety of compounds with known endogenous breath VOCs approaching 900 known compounds. Although there is great diversity of compounds, most are present in relatively low concentrations. One principal interferent in breath is the presence of water which is typically concentrated at 4-5% in breath as compared to ppb concentrations for most VOCs. Therefore, removal of water from breath represents a critical aspect in the design of a breath sensor. Small pore size molecular sieves are a crucial desiccant technology to remove water from the breath rapidly.

In some embodiments, the mouthpiece 102 may further include a filter (not shown) within the body conduit 103. The filter may be operable to remove particles from the air flow before the air flow sample reaches the biosensor. For example, the filter may be a size selective filter to limit larger particles from entering the device.

In some embodiments, the mouthpiece 102 may further include a mouthguard operable to prevent the user from overshooting the mouthpiece. The mouthguard may facilitate used of the device by a user that is unfamiliar with the device. The mouthguard may allow an unfamiliar user to use the device quickly and easily while minimizing any mistakes by the user.

In additional embodiments, the body comprises a first housing and a second housing, and wherein the first housing snap fits to the second housing to form the body.

In an embodiment, the mouthpiece 102 is disposable. This provides the benefit of reducing cross-contamination between users, as each user has their own mouthpiece. In addition, it can speed up testing of multiple users using the same cassette with the same biosensor with different mouthpieces.

In some embodiments, the RTB device may include dual chambers. In an embodiment, the mouthpiece acts as the first chamber. The first chamber may collect exhalate and perform preprocessing to "bring out" the VOCs. In some embodiments, this may be performed by utilizing a polymeric membrane composite that provides the selectivity of the VOCs that are eventually determined to be present in the exhalate of a patient. The pre-processed input gases may feed into the second chamber. In some embodiments, the cassette with the biosensor may act as the second chamber.

In an embodiment, the mouthpiece may further include a breath sample preprocessor to preprocess the breath sample.

Cassette and Biosensor

Figure 7A:
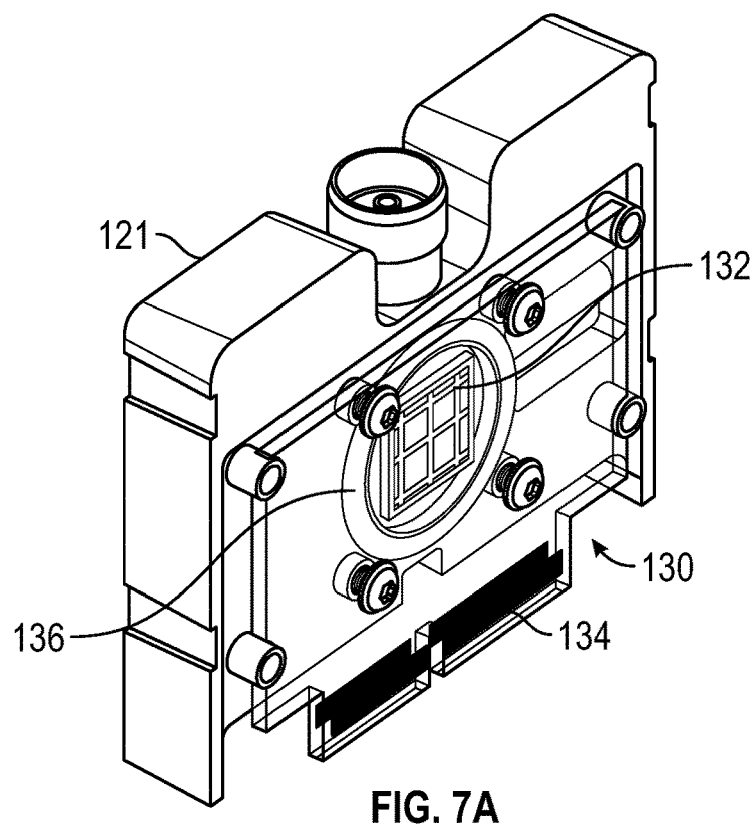
FIG. 7A is a cassette with a biosensor connected to a flow path housing in one example.
Figure 7B:
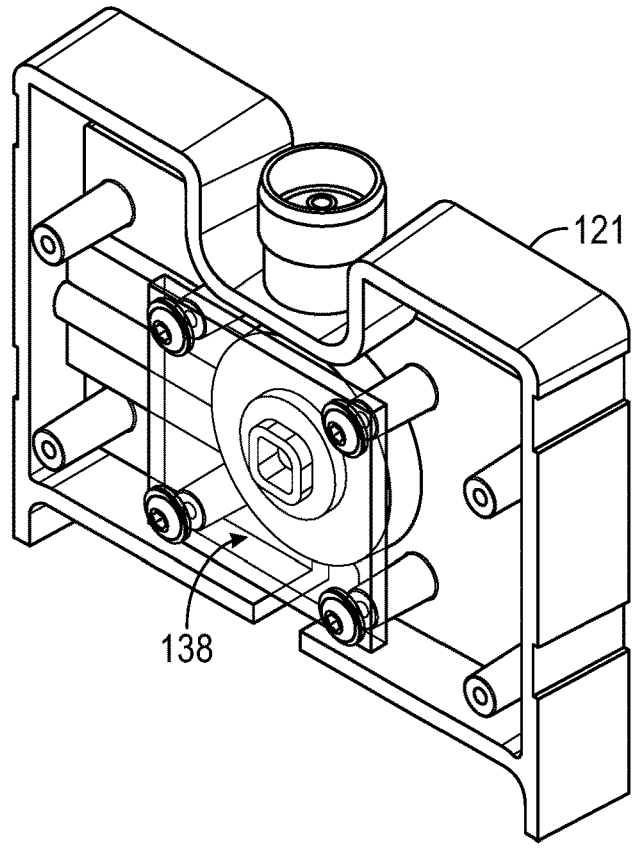
FIG. 7B is a cassette with a UV radiation source connected to a flow path housing in one example.
Figure 8:
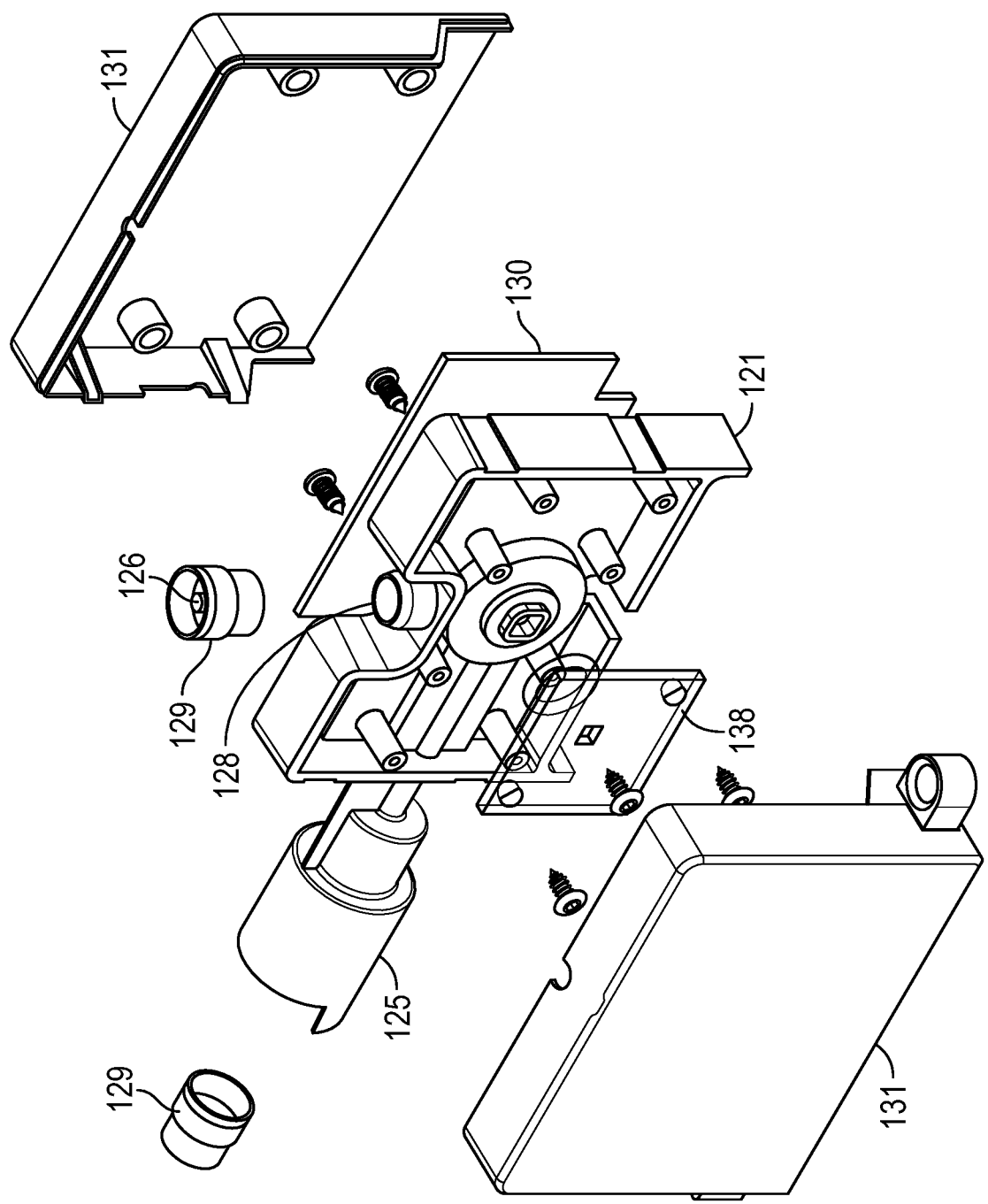
FIG. 8 is a breakout view of a cassette in one example.

Referring to FIGS. 4-8, the rapid breath testing system 100 includes a reusable cassette 120 that includes one or more biosensors 130. In an embodiment, the cassette 120 includes a biosensor 130 having a plurality of graphene-based sensors and a cassette conduit 127 having a cassette inlet 122 and a cassette outlet 128. The biosensor 130 is operable to detect a presence of at least one volatile organic compound (VOC) in an air flow sample through the plurality of graphene-based sensors. The cassette 120 may include a flow path housing 121 that forms the cassette conduit 127, where the air flow sample passes through the cassette conduit 127 and over the biosensor 130. The biosensor 130 and a UV radiation source 138 may be connected to the flow path housing 121 such that the biosensor and/or UV radiation source are in communication with the analysis chamber 123 of the cassette conduit 127. As seen in FIG. 8, the cassette 120 may further include a cover 131 to enclose the flow path housing 121, the biosensor 130, and the UV radiation source 138. The cover 131 may be composed of two parts. In some examples, the cassette inlet 122 and cassette outlet 128 may extend out of the cover. In another example, the cover 131 may include an opening that is fluidly connected to the cassette outlet 128 and/or valve housing 129, such that the cassette outlet 128 remains in the cover 131 but the sample air flow is able to exit out of the cassette 120.

In some examples, the biosensors may be modular sensors that may be removable from the RTB device. The cassette 120 may be reusable for a set number of users before the cassette 120 may be swapped for a new cassette. In some embodiments, the cassette 120 may be reset and/or sterilized between users and may prevent cross-contamination between users. The cassette and/or the biosensor may be disposable or may be reusable for a set number of uses.

The RTB device 100 is designed to provide interchangeability of its cassette 120 and biosensor(s) 130 in order to adapt to the detection of changing bio-signatures due to multiple uses with multiple users, a new VOC, a new permutation of existing pathogens, or new virus profiles. This flexibility allows the RTB device platform to not have to be re-tooled, redesigned or rebuilt for such occurrences. But simply be re-deployed with a cassette with one or more biosensors tuned to the configuration for the particular VOC/bio-signature desired to be detected.

Due the rapid cycling of the RTB device 100, a cassette 120 may enable rapid in field swapping of expired biosensors. Chemiresistive sensors are known to experience long-term baseline drift and other aging effects. In some embodiments, the cassette 120 may include a desiccant (see FIGS. 10-15). The desiccant has a finite capacity for water and must be replaced on a semi-regular basis or recharged, which is difficult in the field. A cassette design minimizes these concerns and also enables future swapping of chemistry in the field as need for different applications. The cassette also eliminates long term cross-contamination.

Figure 4:
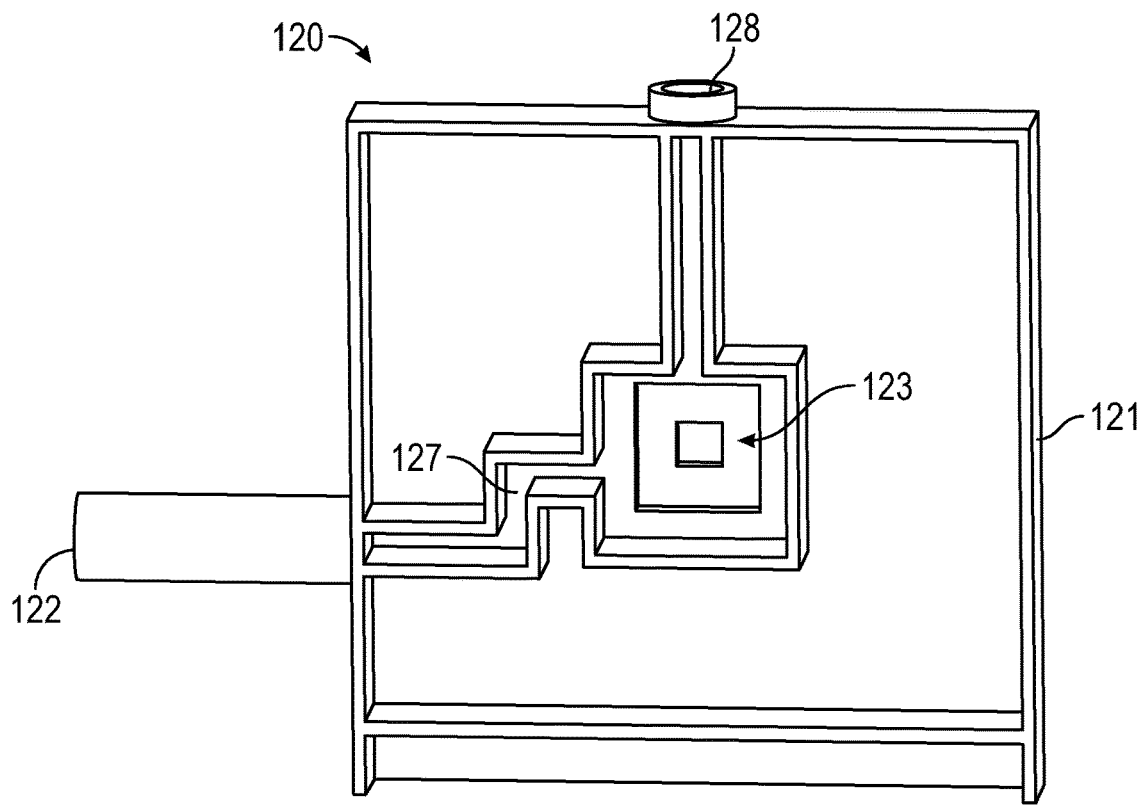
FIG. 4 is a flow path housing of a cassette in one example.
Figure 5:
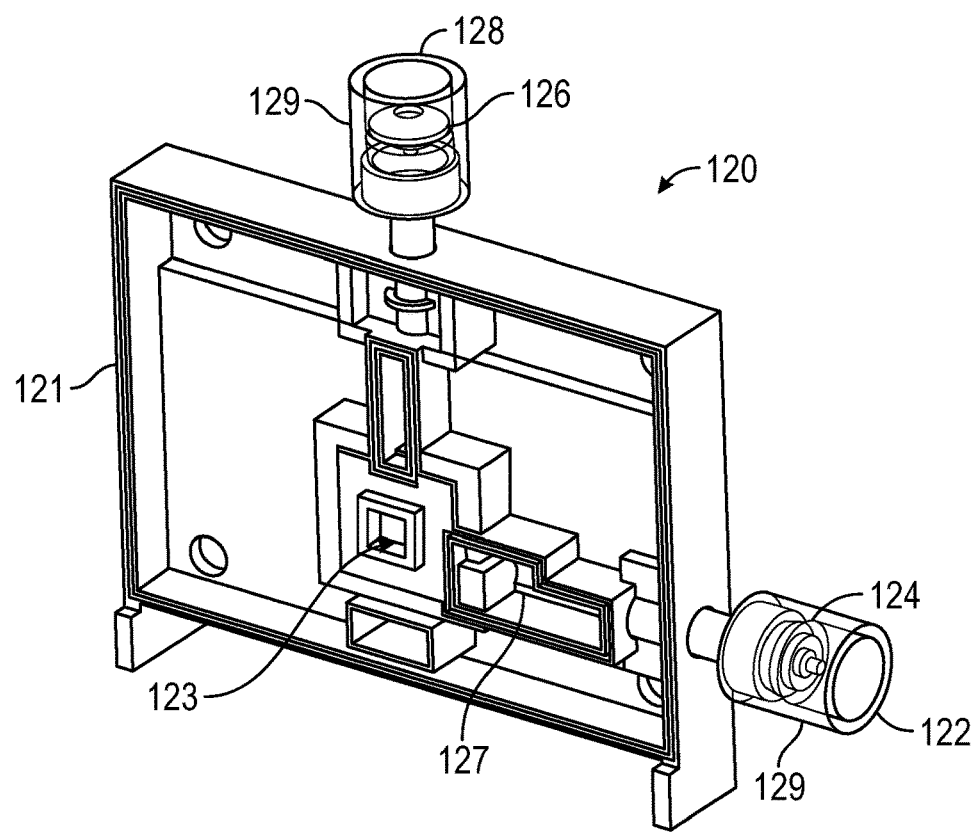
FIG. 5 is a flow path housing of a cassette with valves in one example.
Figure 6A:
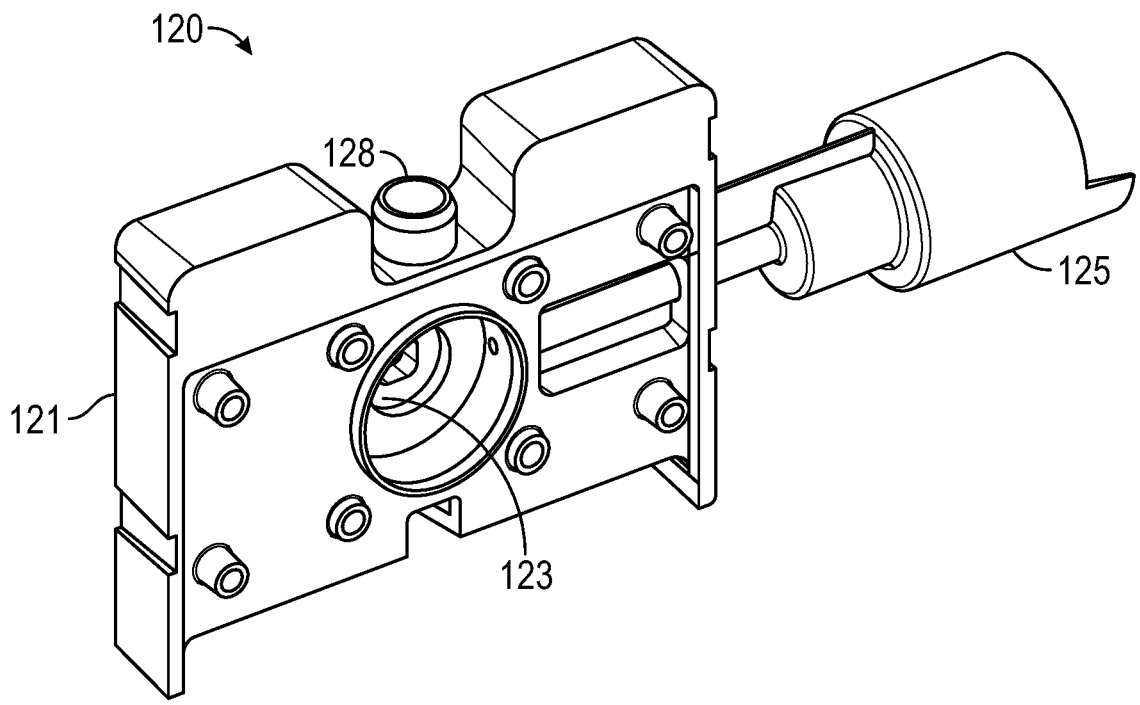
FIG. 6A is a flow path housing in one example.
Figure 6B:
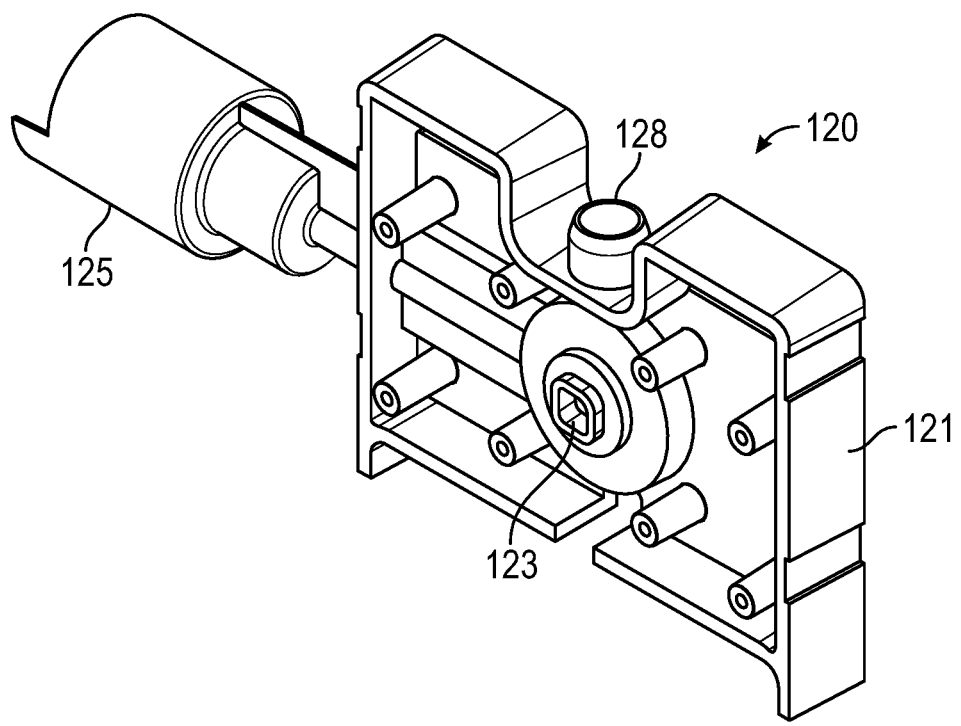
FIG. 6B is a flow path housing in one example.

Referring to FIGS. 4-6B, the cassette comprises a flow path housing 121 defining the cassette conduit 127, the cassette inlet 122, and the cassette outlet 128. FIGS. 4 and 5 are cross-sectional views of the flow path housing 121. FIG. 6A shows a first side of the flow path housing 121 and FIG. 6B shows a second side of the flow path housing 121. The cassette inlet 122 may be located on a first edge of the flow path housing 121 of the cassette 120 and the cassette outlet 128 may be located on a second edge of the flow path housing 121 of the cassette 120. In an example, the cassette conduit 127 has at least one 90° turn from the cassette inlet 122 to the cassette outlet 128.

Additionally, the body conduit 103 of the mouthpiece and/or the cassette conduit 127 of the cassette 120 may be chemically resistant to prevent binding of VOCs to the portions of the device in the flow path and not the biosensor. Anti-viral and/or antimicrobial coatings may also be used to limit infectious compounds to the user.

In an embodiment, the flow path housing 121 includes an extender 125 operable to extend the cassette inlet 122. In some examples, the extender 125 has a tab extending downward from the cassette inlet 122. The tab may be operable to support the cassette 120 when inserted into a base 140 (see FIG. 2).

As seen in FIGS. 4-6B, the cassette 120 may include an analysis chamber 123 operable to receive the breath sample. The analysis chamber 123 may be connected to or part of the cassette conduit 127. In some embodiments, the cassette conduit 127 comprises an analysis chamber 123 having a wider diameter than a diameter of the cassette conduit 127 before and after the analysis chamber. For example, the analysis chamber 123 may be cylindrical, square, or rectangular.

In an embodiment, the flow path housing 121 is open on a first end and a second end of the analysis chamber 123. The biosensor 130 may be adjacent to the first end of the analysis chamber such that it is exposed to the air flow sample flowing through the analysis chamber 123 and forms a seal on the first end of the analysis chamber 123. In some examples, as seen in FIG. 7A, an O-ring 136 may be used to form a seal between the biosensor 130 and the analysis chamber 123.

A reduced volume of breath air flow received at the mouthpiece 102 may flow through the check valve 110 in the body conduit 103 of the mouthpiece 102, through the sample air flow outlet 108, and into the cassette inlet 122 before passing through a first check valve 124 of the cassette 120, the cassette conduit 127, past the biosensor 130 in the analysis chamber 123, and through the second check valve 126, before exiting through the cassette outlet 128. The mouthpiece 102 allows for the reduced volume of breath air flow (air flow sample) to pass over the one or more biosensors 130 in the cassette 120 to detect one or more VOCs in the breath. In some examples, reduced volume of breath air flow may be 1% to 15% of the volume of the breath. The reduced volume of breath air flow over the biosensor may limit the amount of VOC the sensor is exposed to, prolonging the biosensor's life. In addition, the graphene-based sensors may be sensitive enough to detect the VOC in the reduced volume of breath air flow.

Based on the binding energy of different VOCs, there is the potential for residual VOCs to be left on the biosensor. Either UV light or thermal excitations can be used to remove residual VOCs to refresh the sensor. UV light has the additional benefit of acting as a disinfectant mechanism for any potential infectious material which may have reached the sensor. UV light may also be used to enhance sensor kinetics and sensitivity via in situ excitation.

In some embodiments, the cassette 120 further includes a UV radiation source 138 configured to emit UV radiation towards the biosensor 130 to remove at least a portion of VOC bound to the biosensor 130. In some examples, the UV radiation source 138 is adjacent to the second end of the analysis chamber 123, opposite the biosensor, such that the UV radiation passes through the analysis chamber and onto at least a portion of the biosensor and forms a seal on the second end of the analysis chamber. In one example, the UV radiation source may be an LED diode. Optionally, the cassette 120 may further include a heater operable to remove the at least a portion of the VOC bound to the biosensor. The heater may be used in combination with the UV radiation source. The UV radiation source and/or the heater may be operable to unbind any bound VOC, thus resetting the biosensor. In some examples, as seen in FIG. 7B, an O-ring may be used to form a seal between the UV radiation source 138 and the flow path housing 121.

Another aspect of the RTB device is the use of valving to control the flow of breath within the device. One aspect is to limit the amount of analyte the sensor is exposed to to prolong the biosensor's life. Another effect of the valving is to control the section of breath which is analyzed. Yet another effect of the valving is to prevent backflow through the RTB device to limit any potential exposure to the breath or any VOCs that could potentially remain from a previous user. As endogenous VOCs are principally located in the end tidal breath, valving systems can either limit the sampling of the user's breath either spatially or temporally. Valving may be active systems controlled by the concentration of several known breath analytes to identify a threshold for pass-through to the sensor. Alternatively, passive valves with different pressure thresholds may be used to limit the sensor exposure.

Referring to FIG. 5, the cassette 120 may have a first check valve 124 at the cassette inlet 122 and a second check valve 126 at the cassette outlet 128. The check valves are operable to limit flow to one direction through the cassette conduit 127. This further prevents cross-contamination between users. At least one of the first check valve 124, the second check valve 126, or a combination thereof may be an umbrella check valve. In some embodiments, the first check valve 124 and the second check valve 126 are contained within valve housings 129. The valve housing 129 may be connected to or integral with the cassette inlet 122 and/or the cassette outlet 128.

The cassette 120 may include one or more biosensors 130. A biosensor that is, for example, incorporated into or adjacent the analysis chamber in the cassette 120, may use an array of chemi-resistive and field-effect Microelectromechanical Systems (MEMS) made with nanostructures such as graphene doped to provide correlation of sensor response to the chemical reactions. For example, the biosensor 130 may include a plurality of graphene-based sensors. No single MEMS sensor may be specific to any individual VOC, but the combination of MEMS sensors may provide signature responses for the relevant VOCs. In an example, the combination of VOCs may provide the unique biomarker for the relevant infection.

A biosensor, as used herein, can include an applicable number of graphene-based sensors for detecting one or more specific VOCs. Specifically, a biosensor can include four or five different graphene-based sensors. Alternatively, a biosensor can include 16 different graphene-based sensors. In another example, a biosensor can include 64 different graphene-based sensors.

Subsets of different graphene-based sensors can be grouped together to form the plurality of graphene-based sensors. For example, a biosensor can include 32 different graphene-based sensors. As follows, the graphene-based sensors can be grouped into four subsets of 8 sensors.

Graphene-based sensors that form a plurality of graphene-based sensors of a biosensor can be distinguishable from each other according to applicable characteristics of a graphene-based sensor. Specifically, graphene-based sensors that form a biosensor can be doped with different materials, e.g. different metals. More specifically, graphene-based sensors that form a biosensor can be doped with gold, silver, titanium, platinum, or copper. For example, a first subset of graphene-based sensors can be doped with gold, a second subset of graphene-based sensors can be doped with silver, a third subset of graphene-based sensors can be doped with copper, and a fourth subset of graphene-based sensors can be doped with platinum. In some embodiments, the biosensor may include a fifth subset of graphene-based sensors that are pristine graphene without any doping or deposition of metals.

In doping different subsets of graphene-based sensors in a biosensor with different types of material, varying levels of sensitivity to one or more specific VOCs can be achieved. Specifically, doping the graphene-based sensors with different types of material can alter a fermi level of corresponding graphene-based sensors to achieve varying fermi levels across the different subsets of graphene-based sensors. Specifically, dopant materials can be selected and applied to change a fermi level of a graphene-based sensor within 2 eV of the fermi level of graphene. By achieved varying fermi levels across a plurality of graphene-based sensors, varying sensitivity levels are achieved across the biosensor. Such varying sensitivity levels allows for the creation of different responses in the presence of a target VOC. The use of graphene-based sensors is advantageous as it reduces the amount of sample needed to test for the presence of a VOC and potentially facilitates detection of the VOC with one breath sample. In some examples, the additional subsets of graphene-based sensors and combinations of analysis allow for sensing complex mixtures of VOCs.

The graphene-based sensors of the biosensor may be operable to detect a VOC such as a pathogen or other disease marker present in a user's breath. In some examples, the pathogen may be a virus or bacteria. Non-limiting examples of diseases with VOCs detectable in the breath include cancer, asthma, COPD, kidney dysfunction, and respiratory illness. In some embodiments, the biosensor may be adapted to detect RNA strands of a virus. In at least one example, the virus is the SARS-COV-2 virus.

Graphene based sensors are extremely sensitive with the entire material acting as an active sensing surface. Graphene based sensors have achieved single molecule detection in certain cases. Graphene is also capable of being doped (removal of carbon atoms for other atoms) in low concentrations to enhance response to certain analytes. This ameliorates the concerns about the low concentrations present in the breath. This also enables analysis with a single breath as compared to multiple breaths. Single breath enables rapid cycling of users.

Beyond solving potential sensitivity issues, graphene is capable of being functionalized with a wide variety of chemistry to impart a range of selectivity. While these functionalization ultimately have some degree of cross-sensitivity, integrating the differential response from several sensor elements precludes a one to one covering of the target analyte space. By analyzing the response with supervised and unsupervised algorithms, both classification and regression analyses can be performed.

Graphene sensor chemistry here principally includes inorganic mono or poly-elemental clusters ranging in size from single atom to 100 nanometers in size. Those inorganic clusters can further be modified by introducing chemistry at their surface which alters the binding energies of VOCs. Clusters can occupy a range of oxidation states but here are envisioned as present in reduced form. In some embodiments, multiple inorganic clusters may be present in the biosensor. In other embodiments, different inorganic clusters may exist on the interdigitated electrode device. These inorganic clusters may be present in a range of spatial orientations and relative compositions or a range of poly-elemental alloy clusters with different morphologies.

Measurements of the RTB sensor device may typically be mediated through resistive or field effect type measurements. Graphene is well suited for a sensor array with this type of measurement due to its semi-metallic nature and linear dispersion relation around the Dirac point. The high charge carrier mobility of graphene will minimize the energy requirements and enable sensitive measurements. As VOCs interact with the surface of graphene, inorganic clusters or their interfaces, the ability for charge carriers to migrate through graphene may be modified, which is readable as change in resistance (for resistive measurements) or a change in the FET curve (for FET type measurement). Each of the different kinds of sensor chemistry will cause different changes in the measurements.

Graphene can be doped through a variety of techniques due to its monolayer nature. In particular, the substrate to which graphene is attached modulates the electronic properties. Therefore, a biosensor array may have unmodified graphene monolayers placed on a series of different polymer substrates. This strategy mitigates the need for traditional silicon substrate and enables a wide array of sensor arrays to be developed solely based on the chemical composition of the substrate.

The analysis chamber 123 may be fluidly connected to one or more biosensors 130 having a plurality of graphene-based sensors 132. The analysis chamber 123 of the cassette 120 may comprise a biosensor 130 with an array of nanosensors configured to detect one or more volatile organic compounds. In some embodiments, the array of nanosensors is an array of graphene-based sensors 132. The array may include 16, 32, or 64 graphene-based sensors. In an example, the biosensor includes an array of 64 graphene-based sensors of which a minimum of 16 is used for each analysis.

In an embodiment, the biosensor 130 includes a plurality of subsets of graphene-based sensors 132 of the plurality of graphene-based sensors and each subset of graphene-based sensors of the plurality of subsets of graphene-based sensors is doped with a corresponding different type of metal of a plurality of different types of metal or may be undoped graphene. The plurality of different types of metal may include at least two of pristine graphene, gold, silver, titanium, platinum, and copper. In an example, each subset of graphene-based sensors of the plurality of subsets of graphene-based sensors is configured to generate a different characteristic response in a physical presence of the VOC. In another example, each graphene-based sensor in a corresponding subset of graphene-based sensors is configured to generate a same characteristic response in the physical presence of the VOC. The VOC may be detected based on different characteristic responses generated by the plurality of subsets of graphene-based sensors in the physical presence of the VOC.

In some embodiments, each subset of graphene-based sensors of the plurality of subsets of graphene-based sensors is doped with a different element or undoped graphene. The different elements change a fermi level of graphene of each subset of graphene-based sensors to corresponding different changed fermi levels. For example, each of the corresponding different changed fermi levels may be within 2 eV of the fermi level of the graphene.

In an embodiment, the plurality of subsets of graphene-based sensors may include four different subsets of graphene-based sensors that are configured to generate a different characteristic response in a physical presence of the VOC. In an example, the four different subsets of graphene-based sensors may each include four graphene-based sensors. In another embodiment, the plurality of subsets of graphene-based sensors may include five different subsets of graphene-based sensors, where one of the subsets graphene-based sensors is pristine graphene without any doping or deposition of metals.

Referring back to FIG. 7A, the biosensor 130 may include a chip 134 operable to detect bio-signatures of the breath sample in the analysis chamber 123. In some embodiments, the biosensor may be coupled to a processor configured to receive a signal that is indicative of an occurrence of at least one VOC binding to the biosensor. The cassette and/or biosensor may include a processor configured to communicate detection of a VOC to a wireless device, a base, and/or an indicator on the device. In some examples, the biosensor may include two or more biosensors and the biosensors may share an electronics card comprising a processor. In other examples, the cassette and/or biosensor may include 2 or 3 electronics cards and/or processors. The cassette and/or biosensor may be operable to switch between the different biosensors in use or may use multiple biosensors at a time to increase the sensitivity of the RTB device. The biosensors may be reset between device usage or reset all at the same time. Alternatively, the processor may be located in the base and the cassette may be placed into the base for analysis.

The biosensor chip may be configured to measure relative change of current or resistance that is correlated to the concentration of a VOC that is desired to be detected. In some embodiments, the channels of the graphene-based sensors will manifest a response pattern that will form the basis of a characterization for the VOC (e.g., pathogen infected compounds).

The biosensor may further comprise a tracking device configured to monitor use of the biosensor, and, in response to one or more statistics associated with the use, control a resetting or a disabling of the biosensor. An important aspect of the RTB device is that by design it requires limited training of operators. Accordingly, the RTB is designed to enable easy swapping of mouthpieces and/or cassettes. Also, since the biosensor is performing chemical reactions, it may have a limit to the number of samples that can be accurately analyzed. Therefore, the cassette or biosensor may include a mechanism to prevent the operator from using past its useful life. Therefore, the biosensor may be operable to (i) track the number of cycles it has been used and (ii) have a self-disabling feature to prevent use beyond those cycles. This feature may be, for example, a fuse that gets blown after a certain amount of use.

In some embodiments, the RTB device also includes a sensor sanitizer to sanitize the cassette, and one or more environment condition sensors to sense at least one of pressure, humidity or temperature. The processor may be configured to calibrate the biosensor or the results in accordance with measurements of the one or more environment condition sensors.

Base

Figure 9:
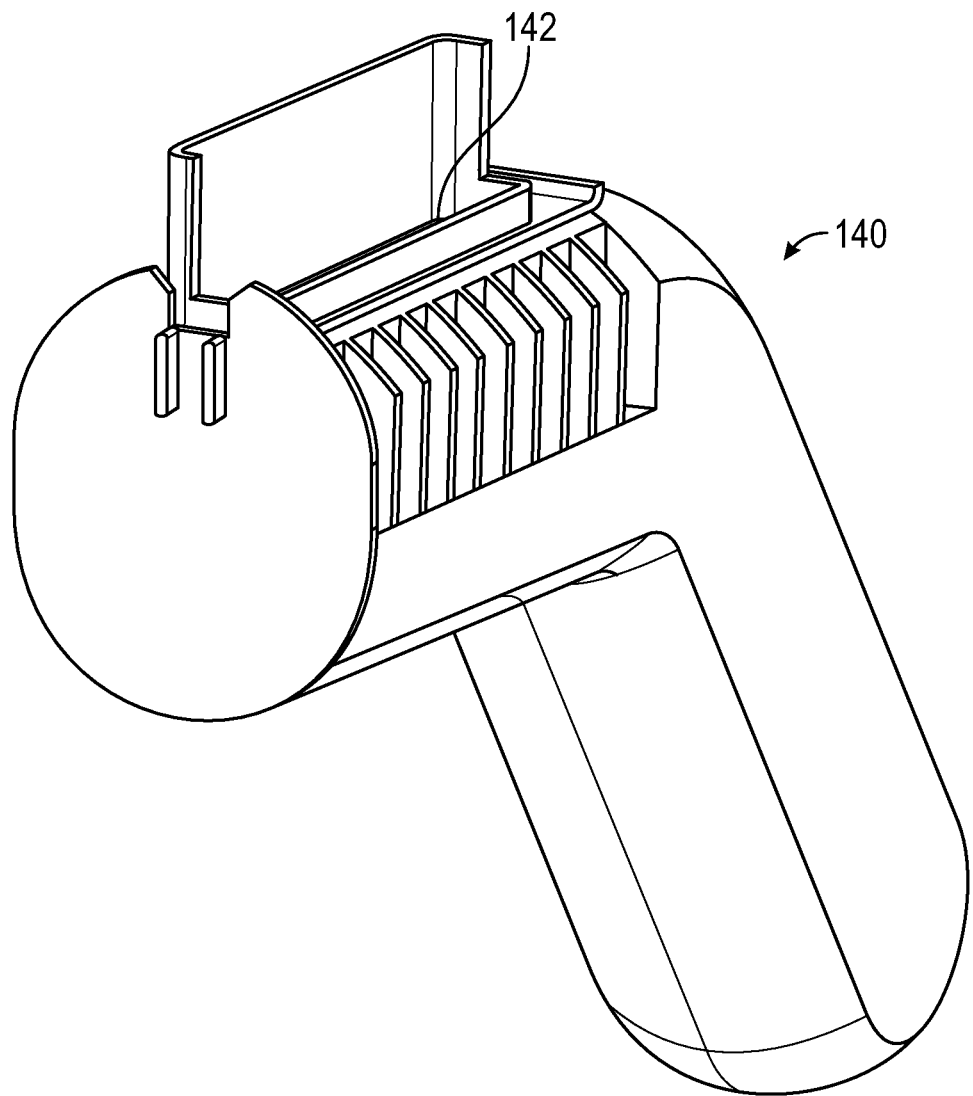
FIG. 9 is body of a rapid breath testing system in one example.

As seen in FIGS. 2 and 9, the rapid breath testing system 100 further includes a base 140 operable to receive the cassette 120. In some embodiments, the base 140 may be handheld, making the rapid breath testing system 100 handheld and portable.

The base 140 is configured to receive the cassette 120 in a removable manner such that when the cassette 120 is disposed in the base 140, the cassette inlet 122 of the cassette conduit 127 is directly coupled to a sample air flow outlet 108 of the mouthpiece 102 to form a flow path for the air flow sample that extends from the mouthpiece 102 through the cassette 120 and is physically isolated from all portions of the base 140.

The cassette 120 is configured to be sanitized or reset separate from the base 140 after one or more uses of the cassette 120 during one or more testing phases of the rapid breath testing system 100 while the cassette 120 is coupled to the base 140. In some examples, the cassette 120 may also be coupled to the mouthpiece 102 while being sanitized or reset.

The base 140 comprises a connector having a single direction track 142 for receiving the cassette 120. This allows for easy installation of the cassette within the base without any training.

In an embodiment, the base includes one or more processors. The base further includes a computer-readable medium comprising instructions stored therein, which when executed by the one or more processors, cause the one or more processors to collect data generated from the biosensor after contact with the at least one VOC, store the data in a memory, analyze the data to make a determination whether the VOC is present in the sample air flow; and facilitate transmission of a result of the determination.

The biosensor electronically connects to the processor of the base when the cassette is physically coupled to the base.

The instructions which when executed by the one or more processors, cause the one or more processors to transmit either or both the data and results of the determination. Either or both the data and the results of the determination are transmitted via a wireless personal area network (PAN) to a mobile device. The base includes a battery configured to provide power to the biosensor when the cassette is physically coupled to the base.

The base 140 may further include one or more indicators 144 that are perceivable by a user and the one or more indicators 144 are operable to indicate to the user if a VOC is detected. In an example the one or more indicators 144 may be one or more LEDs. For example, as seen in FIG. 2, the base 140 may include three LED indicators. Each indicator may represent a different state of the biosensor (e.g. positive result, negative result, device reset or clear for use, etc.).

Methods

Further provided herein is a method for detecting at least one VOC in an air flow sample. The method may include receiving an air flow from a breath passed into a breath inlet of a mouthpiece of a rapid breath testing system, the rapid breath testing system further comprising a cassette comprising a biosensor connected to the mouthpiece. A sample of the air flow passes from a sample air flow outlet of the mouthpiece through a cassette conduit of the cassette. The method further includes detecting, through a plurality of graphene-based sensors of the biosensor, at least one VOC in the air flow sample. Backflow of the air flow is prevented or minimized using one or more check valves. The one or more check valves may be within the mouthpiece and/or the cassette. In some examples, the one or more check valves may be an umbrella check valve.

In various embodiments, 80% to 99% of the air flow from the breath entering the breath inlet exits through an exhaust of the mouthpiece and any remaining air flow is the air flow sample. In some examples, 80%, 85%, 90%, 95%, or 99% of the air flow from the breath exits the exhaust of the mouthpiece.

The method may further include connecting the mouthpiece to the cassette prior to receiving the air flow, connecting the cassette to a base that is configured to receive the cassette in a removable manner, sending data from the biosensor after contact with the at least one VOC to a processor in the base, storing and analyzing the data to determine a presence of the at least one VOC in the sample air flow, providing an indicator on the base if the at least one VOC is detected, transmitting either or both the data and a result of a determination of a presence of the at least on VOC in the sample air flow to a mobile device, resetting the biosensor after receiving the sample air flow, applying heat to at least a portion of the biosensor while transmitting the UV light, and/or replacing the mouthpiece with a second mouthpiece. Resetting the biosensor may include transmitting UV light onto at least a portion of the biosensor to release any bound VOC from the biosensor.

Alternative Embodiments

Figure 10:
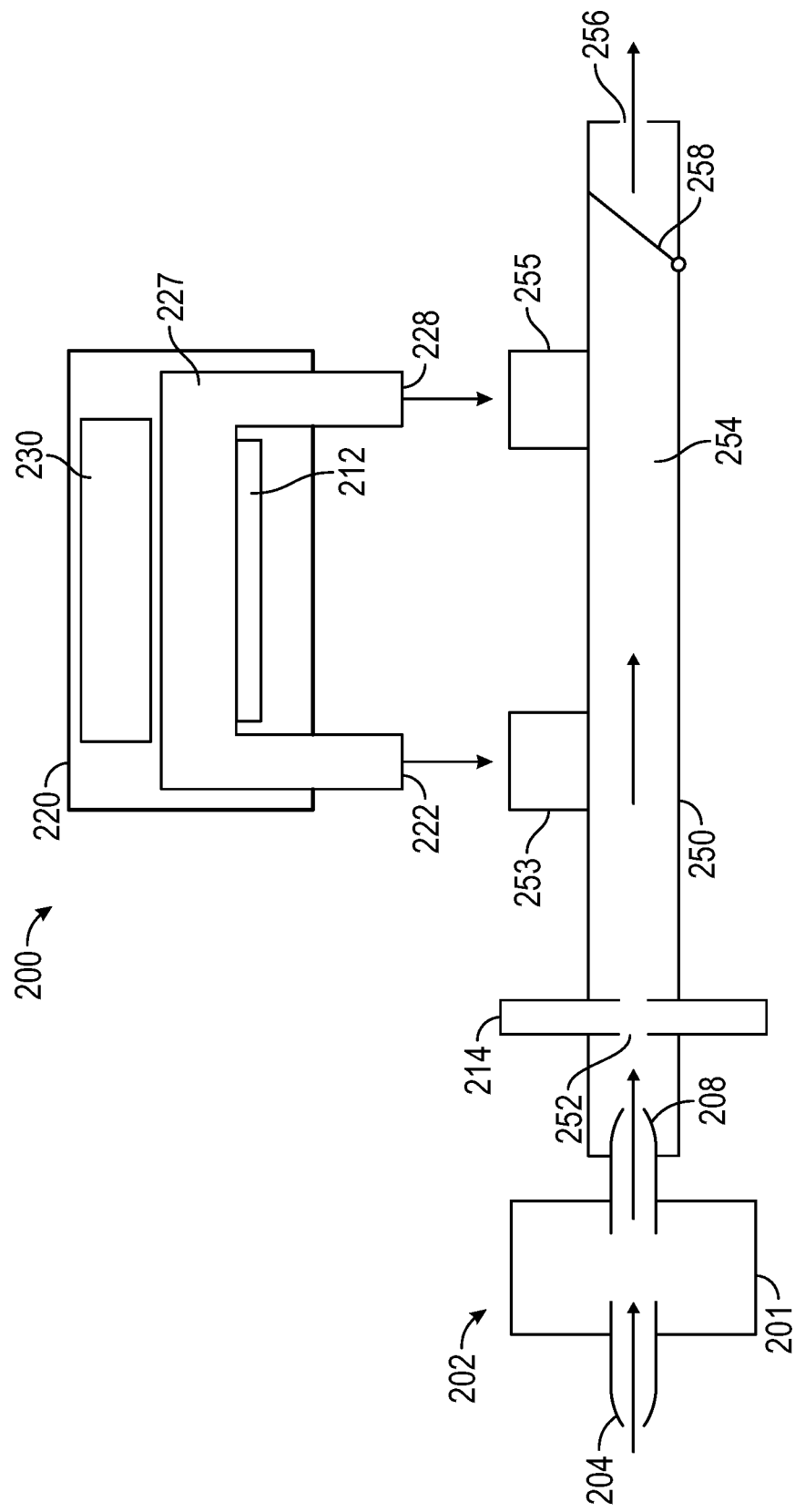
FIG. 10 is a rapid test breathalyzer in one example.

FIG. 10 is an example rapid test breathalyzer 200 that includes a baffled mouthpiece 202 with a mouthpiece body 201, an inlet 204, and an outlet 208; a device body 250 with a conduit 254, an inlet 252, an outlet 256, a filter 214, a first cassette connector 253, a second cassette connector 255, and a passive exit valve 258; and a cassette 220 with a biosensor 230, a desiccant 212, and a cassette conduit 227. The cassette conduit 227 includes a cassette inlet 222 operable to connect to the first cassette connector 253 and a cassette outlet 228 operable to connect to the second cassette connector 255 on the device body 250 to connect the conduit 254 of the device body 250 with the cassette conduit 227. The cassette 220 may be operable to push connect to the device body 250. For example, push connect valves may be used to connect the cassette 220 to the device body 250. The first and second cassette connectors may be female piping operable to connect to the device body conduit 254 and the cassette inlet 222 and the cassette outlet 228 may be male pipe leads protruding out of the cassette 220. This gives the operator obvious direction in how to connect the cassette 220 into the device body 250. About 95% of the air flow from a breath received at the mouthpiece 202 may flow through the conduit 254 of the device body 250, through the passive exit valve 258, and out the device at a device outlet 256 without flowing through the cassette 220. About 5% of the air flow may pass from the conduit 254 of the device body 250, through the cassette inlet 22, the cassette conduit 227, and the cassette outlet 228, before passing back into the conduit 254 of the device body 250, through the passive exit valve 258 and out the outlet 256 of the device body 250. The cassette 220 allows for the reduced volume of breath air flow to pass over the one or more biosensors 230 in the cassette 220 to detect one or more VOCs in the breath. This device configuration provides a sturdy connection to the system, makes it harder to alter results, and keeps most components in the system.

Figure 11:
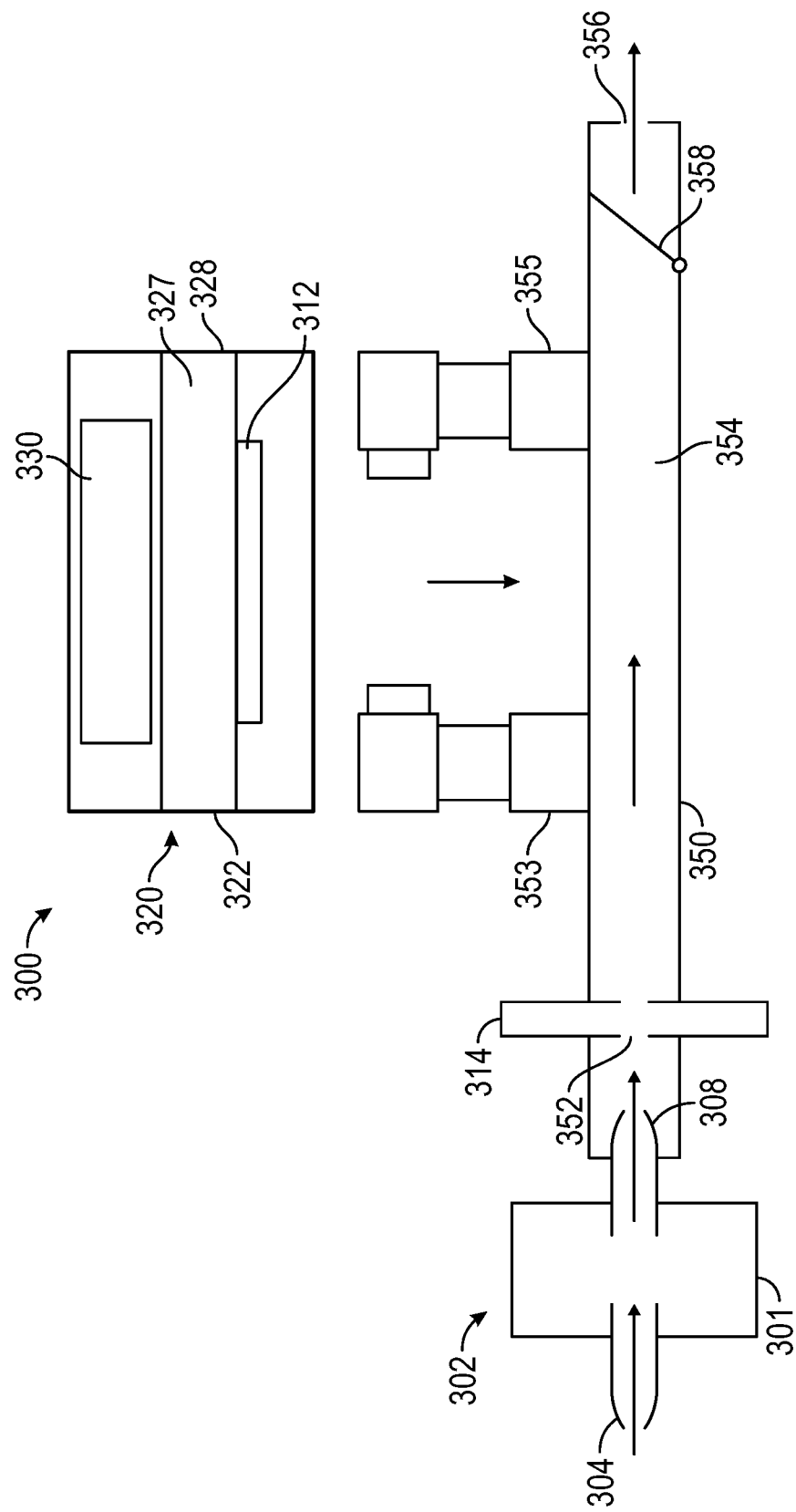
FIG. 11 is a rapid test breathalyzer in one example.

FIG. 11 is an example rapid test breathalyzer 300 that includes a baffled mouthpiece 302 with a mouthpiece body 301, an inlet 304, and an outlet 308; a device body 350 with a conduit 354, an inlet 352, an outlet 356, a filter 314, a first cassette connector 353, a second cassette connector 355, and a passive exit valve 358; and a cassette 320 with a biosensor 330, a desiccant 312, and a cassette conduit 327. The cassette conduit 327 includes a cassette inlet 322 operable to connect to the first cassette connector 353 and a cassette outlet 328 operable to connect to the second cassette connector 355 on the device body 350 to connect the conduit 354 of the device body 350 with the cassette conduit 327. The cassette 320 may be operable to slide in to connect to the device body 350. About 95% of the air flow from a breath received at the mouthpiece 302 may flow through the conduit 354 of the device body 350, through the passive exit valve 358, and out the device at a device outlet 356 without flowing through the cassette 320. About 5% of the air flow may pass from the conduit 354 of the device body 350, through the cassette inlet 322, the cassette conduit 327, and the cassette outlet 328, before passing back into the conduit 354 of the device body 350, through the passive exit valve 358 and out the device body 350. The cassette 320 allows for the reduced volume of breath air flow to pass over the one or more biosensors 330 in the cassette 320 to detect one or more VOCs in the breath. For this configuration of the cassette 320, the device body 350 is as compact as feasibly possible. Connections protrude from inside the device body and create a slot for the operator to insert the cassette, thus creating horizontal connections. Therefore the cassette inlet 322 and outlet 328 to the cassette conduit 327 may be located on opposite sides of the cassette 320. The cassette is compact, using as little waste as possible, such that the user is only throwing out parts that are expendable. The cassette requires minimal force to be inserted into the device body.

Figure 12:
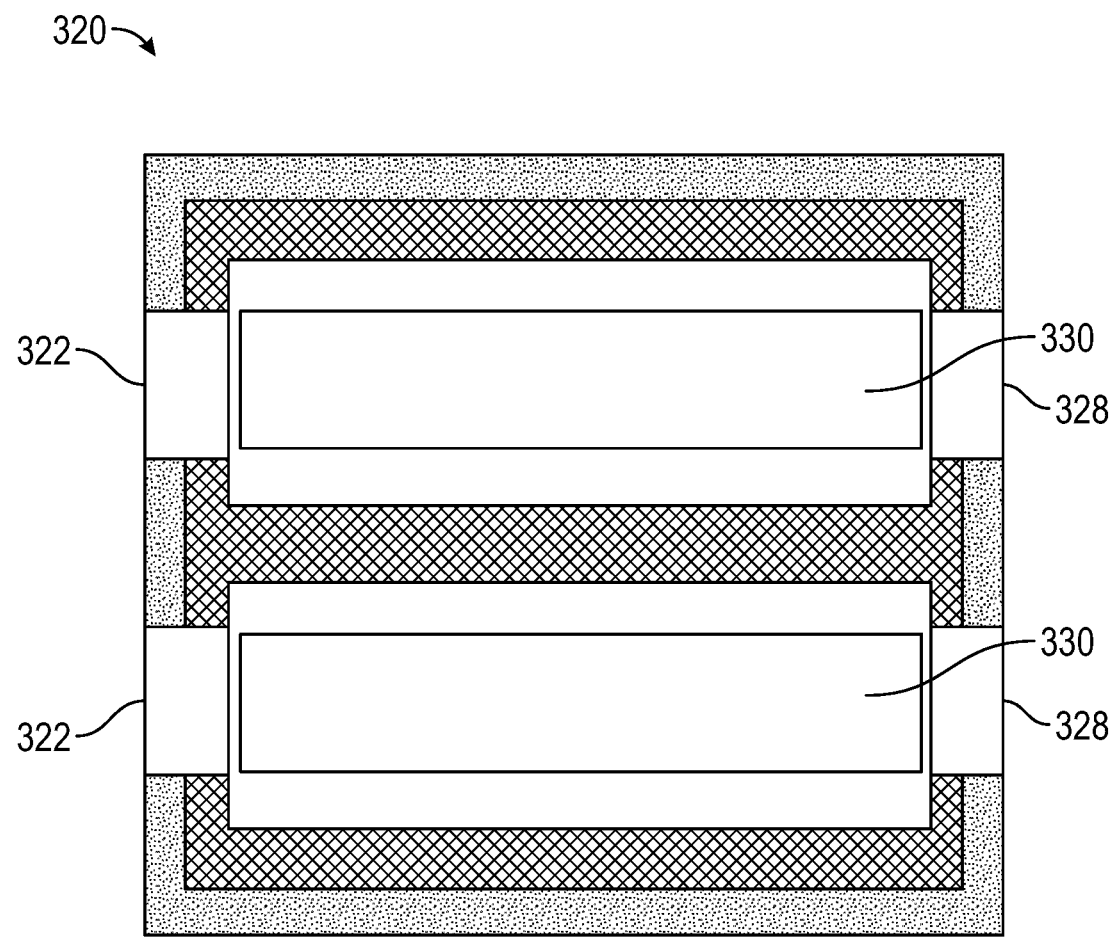
FIG. 12 is a rapid test breathalyzer cassette with two biosensors in one example.

In some examples, the cassette may have multiple chambers for holding multiple biosensors, desiccants, and/or processors. FIG. 12 is an example cassette 320 with multiple chambers that includes two biosensors 330 and two cassette conduits with two cassette inlets 322 and two cassette outlets 328. The air flow may be directed to one of the biosensors using a Y-connector. LED lights connected to the chip may light up when a particular chamber is active. In some examples, the cassette with multiple chambers may include more than one chip or may include only one chip.

Figure 13:
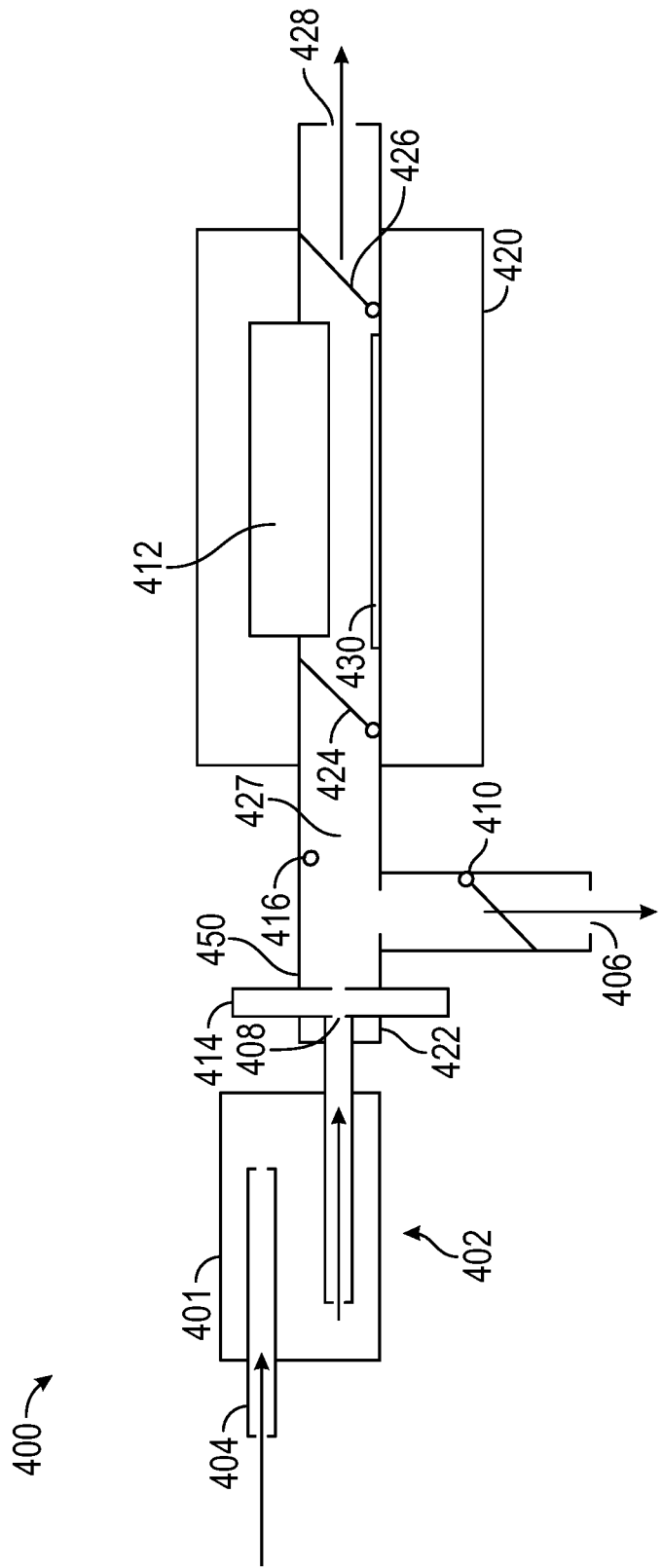
FIG. 13 is a rapid test breathalyzer in one example.

FIG. 13 is an example rapid test breathalyzer 400 that includes a baffled mouthpiece 402 with a mouthpiece body 401, an inlet 404, and an outlet 408; and a device body 450 with an inlet 422, a conduit 427, a biosensor 430, a passive entrance valve 424, a passive exit valve 426, an outlet 428, and a waste conduit 406. The device 400 may optionally include a filter 414, a breath sensor 416, and a desiccant 412. A portion of the air flow from a breath received at the mouthpiece 402 may flow through the conduit 427 of the device body 420, through a passive or active bypass valve 410, through the waste conduit 406, and out the device without flowing past the biosensor 430. Another portion of the air flow may pass through the conduit 427 of the device body 420, through the passive entrance valve 424, past the biosensor 430 and desiccant 412, before passing through the passive exit valve 426 and out the outlet 428 the device 400. The reduced volume of breath air flow passes over the one or more graphene-based sensors in the biosensor 430 to detect one or more VOCs in the breath.

Figure 14:
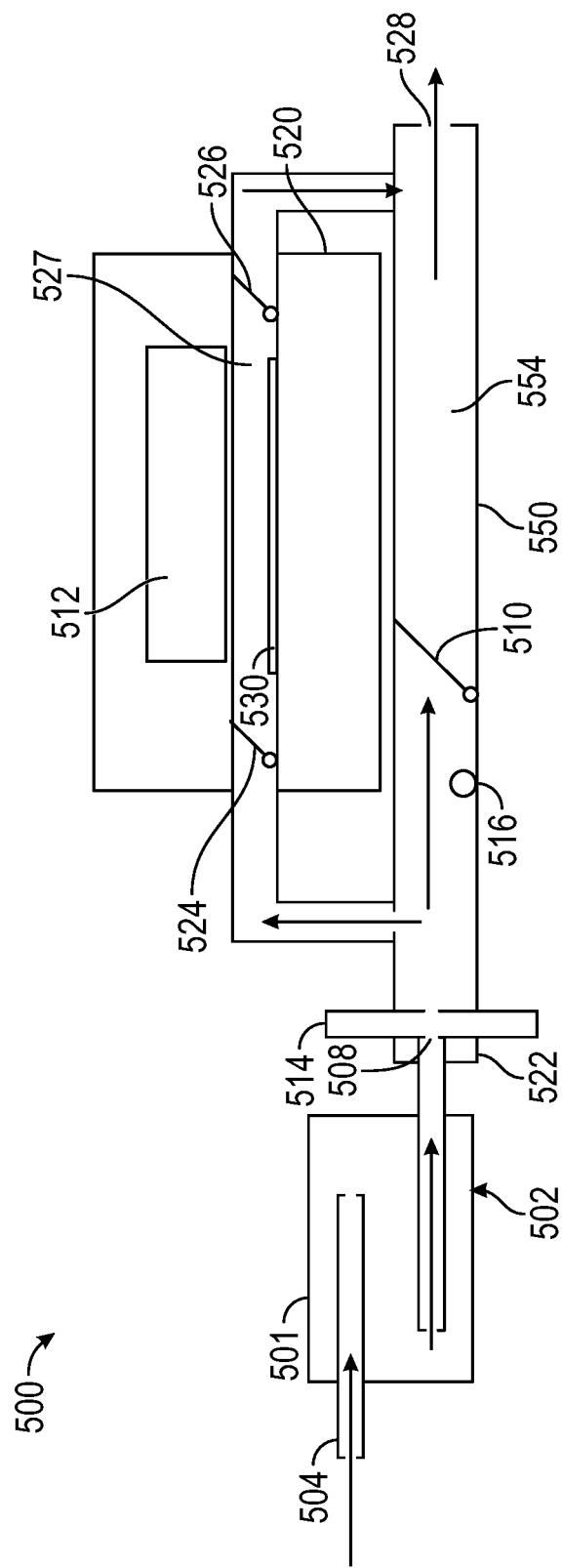
FIG. 14 is a rapid test breathalyzer in one example.

FIG. 14 is an example rapid test breathalyzer 500 that includes a baffled mouthpiece 502 with a mouthpiece body 501, an inlet 504, and an outlet 508; a device body 550 with a conduit 554, a cassette inlet 522, a cassette outlet 528, a breath sensor 516, and a passive bypass valve 510; and a cassette 520 with a biosensor 530 and a cassette conduit 527 with a passive entrance valve 524 and an exit valve 526. The device 500 may optionally include a filter 514 and a desiccant 512. The cassette conduit 527 is connected to the cassette inlet 522 and the cassette outlet 528 and connects the conduit 554 of the device body 550 with the cassette conduit 527. The cassette may be integral with or permanently attached to the device body. About 90% of the air flow from a breath received at the mouthpiece 502 may flow through the cassette conduit 527 of the device body 550, through the passive bypass valve 510, and out the device 500 without flowing through the cassette 520. About 10% of the air flow may pass from the conduit 554 of the device body 550, through the cassette inlet 522, the passive entrance valve 524, the cassette conduit 527, past the biosensor 530, and through the passive exit valve 526 and the cassette outlet 528, before passing back into the conduit 554 of the device body 550 and out the device 500. The cassette 520 allows for the reduced volume of breath air flow to pass over the one or more graphene-based sensors in the biosensor to detect one or more VOCs in the breath.

Figure 15:
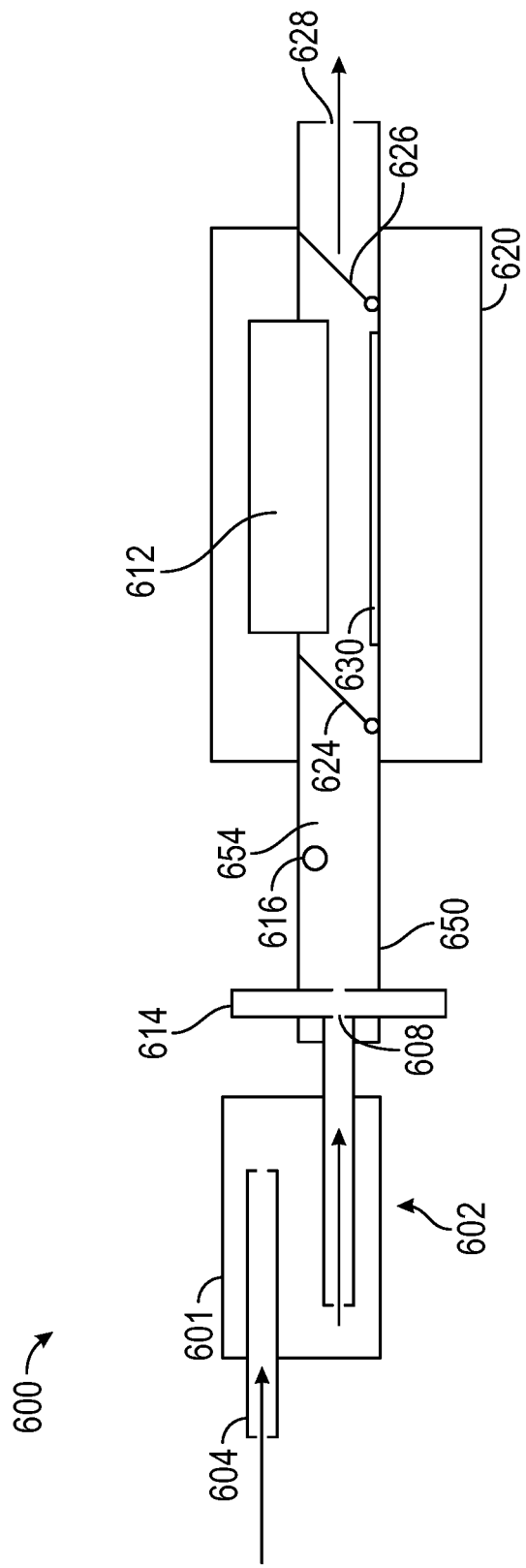
FIG. 15 is a rapid test breathalyzer in one example.

FIG. 15 is an example rapid test breathalyzer 600 that includes a baffled mouthpiece 602 with a mouthpiece body 601, an inlet 604, and an outlet 608; and a device body 650 with a conduit 654, a cassette 620 with a biosensor 630, a passive entrance valve 624, and a passive exit valve 626, and a cassette outlet 628. The device body may optionally include a filter 614, a desiccant 612, and a breath sensor 616. The air flow from a breath received at the mouthpiece 602 may flow through the conduit 654 of the device body 650, through the passive entrance valve 624, past the biosensor 630 and desiccant 612, before passing through the passive exit valve 626 and out the device 600. The volume of breath air flow passes over the one or more graphene-based sensors in the biosensor to detect one or more VOCs in the breath.

Data Analytics

Data analytics may operate through analysis methodologies including but not limited to principal component analysis, support vector machines, or supervised learning methodologies. Non-limiting examples of supervised learning methodologies include principal component analysis, support vector machines, linear discriminant analysis, quadratic discriminant analysis, decision trees, random forest, k nearest neighbors, adaptive boosting, and other supervised learning methodologies known in the art. These schemes may be used for classification but regression based on disease state and other factors may also be used. A variety of sensor metrics may be fed into these algorithms to best classify positive or negative status with respect to the disease. Additionally, the differential weight applied in generating the classification boundary can be used to inform on promising aspects of the sensor to optimize. Classification boundaries can be linear or non-linear and will inherently occur in a high dimensional space. Data acquisition rates and sensor potential bias can be tuned to minimize the effects of sensor drift.

Data analysis can also be handled through neural network methodologies with a variety of architectures and feature engineering efforts.

The RTB device may be operable to collect and analyze the exhalation of a test subject and transmit (e.g. by wireless transmission) the data to a paired mobile device for analysis. The "mobile device" may be a smartphone, tablet computer, or other portable computing device that collects and analyzes the exhalation of a test subject and transmits (e.g. by wireless transmission) the data to a paired mobile device for analysis. The "mobile device" may be a smartphone, tablet computer, or other portable computing.

The device may be connected to the RTB device via Bluetooth™, Wifi, BLE, or other type of network connection, and running a custom application. The custom application, or "custom app" as referred to herein, provides for the mobile device on which it is executing to interface with the RTB device, collect and analyze testing data from one or more mobile devices, provide results to an operator and/or to the RTB device, and transfer data to a server.

The RTB device combines the elements of breath capture, bio-material sensors, and real-time data capture from the disposition of sensors, and on-the-spot results delivery distributed via Bluetooth™ or other network connection to a custom application for the iPhone, Android, or other platform. The simplicity of use and rapid distribution of RTB devices are essential for widespread deployment in support of any widespread testing capability.

In an embodiment, the RTB device includes an integrated breathalyzer interface to the RTB's Restriction of Hazardous Substances (RoHS) compliant housing, the integration of a sensor array into the printed circuit board (PCB) RoHS compliant substrate base, various other sensors, a power distribution system, one or more processors, and a component for communicating between the RTB device and a sensor algorithm and mobile application performing data acquisition via Bluetooth™ or other connection from the RTB device. The RTB includes a breath collection component with the replaceable mouthpiece and one or more swappable biosensor arrays that are "pluggable" for reuse or reconfiguration.

The RTB device may be configured to communicate with an application engine that utilizes a sensor algorithm. An algorithm for the particular response pattern may be selected from a plurality of available algorithms and utilized to produce a readout to an application platform on IOS, Android or other platform. The app residing on either of these platforms may connect via a network connection such as, for example, Bluetooth™. The application engine may be supported on the iPhone and Android platforms to support on-the-spot real time (or near real time) display of sensor data.

In some embodiments, a testing system comprising one or more RTB devices and mobile devices is provided. The system may include one or more "RFID Safe Socializing Bands (SSB)". An SSB may be a wrist worn RFID tag used for tracking the contacts Test Subjects have with other SSB wearing individuals. Embodiments are not limited to wrist worn SSB. In some embodiments, upon a person completing an RTB test, the results and/or a status is encoded in the SSB along with the unique identifier for the RTB device and/or cassette involved in the test.

In some embodiments, a testing system as described above provides for implementing an environment with a controlled zone, a de-militarized zone, and an uncontrolled zone. A "controlled zone" is a physical space to which Test Subjects are allowed access after negative screening results. Screening results are the results of a local algorithm on a mobile device performed on the breath samples of test subjects. A "De-Militarized Zone (DMZ)" is a physical space in which operators perform screening of Test Subjects. An "uncontrolled zone" is a physical space in which personnel are unscreened. Having the screening results of a person tested by an RTB device encoded on an SSB worn by the person, the transition of that person from the DMZ to the controlled area may be automatically authorized and monitored based on the SSB. The monitoring may be by any mobile or other device within the controlled area. The monitoring, with the use of a central server collecting RTB screening results, can be used to alert an operator as to when each person in the controlled area is due for a retest or the like, based for example, on the results of the previous tests of that person. The capability to implement zones using the RTB enables practices that may allow for businesses and buildings to safely operate even during outbreaks of certain airborne pathogens.

Figure 16:
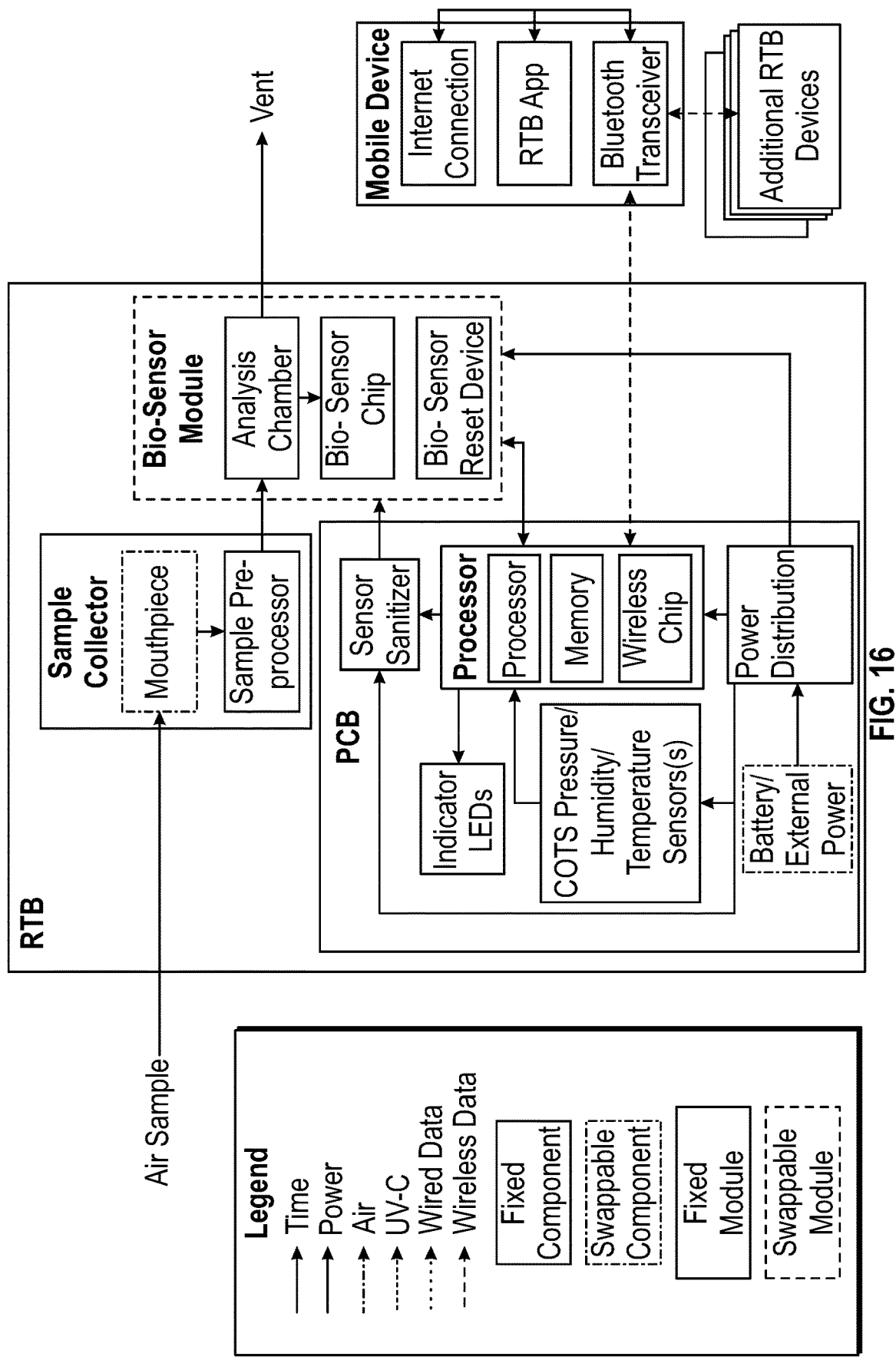
FIG. 16 illustrates a block diagram of a Rapid Test Breathalyzer (RTB) according to some embodiments, and its communication with one or more mobile devices.

FIG. 16 illustrates an example RTB device and a mobile device. The example RTB device includes a breath sample collector and at least one pluggable (swappable) cassette with a biosensor that connects to a plug-in interface on the PCB of the RTB device. A processor and a wireless network interface enables communication between the RTB device and the mobile device. The RTB includes a plurality of indicator lights, and the processor is configured to illuminate one or more of the plurality of indicator lights according to a status of the analysis of the breath sample, and according to messages received from the mobile device.

In the examples described herein, for purposes of explanation and non-limitation, specific details are set forth, such as particular nodes, functional entities, techniques, protocols, standards, etc. in order to provide an understanding of the described technology. It will be apparent to one skilled in the art that other embodiments may be practiced apart from the specific details described below. In other instances, detailed descriptions of well-known methods, devices, techniques, etc. are omitted so as not to obscure the description with unnecessary detail. Individual function blocks are shown in the figures. Those skilled in the art will appreciate that the functions of those blocks may be implemented using individual hardware circuits, using software programs and data in conjunction with a suitably programmed microprocessor or general purpose computer, using applications specific integrated circuitry (ASIC), and/or using one or more digital signal processors (DSPs). The software program instructions and data may be stored on computer-readable storage medium and when the instructions are executed by a computer or other suitable processor control, the computer or processor performs the functions. Although databases may be depicted herein as tables, other formats (including relational databases, object-based models, and/or distributed databases) may be used to store and manipulate data.

Although process steps, algorithms or the like may be described or claimed in a particular sequential order, such processes may be configured to work in different orders. In other words, any sequence or order of steps that may be explicitly described or claimed does not necessarily indicate a requirement that the steps be performed in that order. The steps of processes described herein may be performed in any order possible. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to the technology, and does not imply that the illustrated process is preferred.

Processors, memory, network interfaces, I/O interfaces, and displays noted above are, or includes, hardware devices (for example, electronic circuits or combinations of circuits) that are configured to perform various different functions for a computing device, such as computer.

In some embodiments, each or any of the processors is or includes, for example, a single- or multi-core processor, a microprocessor (e.g., which may be referred to as a central processing unit or CPU), a digital signal processor (DSP), a microprocessor in association with a DSP core, an Application Specific Integrated Circuit (ASIC), a Field Programmable Gate Array (FPGA) circuit, or a system-on-a-chip (SOC) (e.g., an integrated circuit that includes a CPU and other hardware components such as memory, networking interfaces, and the like). And/or, in some embodiments, each or any of the processors uses an instruction set architecture such as x86 or Advanced RISC Machine (ARM).

In some embodiments, each or any of the memory devices is or includes a random access memory (RAM) (such as a Dynamic RAM (DRAM) or Static RAM (SRAM)), a flash memory (based on, e.g., NAND or NOR technology), a hard disk, a magneto-optical medium, an optical medium, cache memory, a register (e.g., that holds instructions), or other type of device that performs the volatile or non-volatile storage of data and/or instructions (e.g., software that is executed on or by processors). Memory devices are examples of non-volatile computer-readable storage media.

In some embodiments, each or any of the network interface devices includes one or more circuits (such as a baseband processor and/or a wired or wireless transceiver), and implements layer one, layer two, and/or higher layers for one or more wired communications technologies (such as Ethernet (IEEE 802.3) and/or wireless communications technologies (such as Bluetooth™, WiFi (IEEE 802.11), GSM, CDMA2000, UMTS, LTE, LTE-Advanced (LTE-A), 5G, and/or other short-range, mid-range, and/or long-range wireless communications technologies). Transceivers may comprise circuitry for a transmitter and a receiver.

It will be appreciated that as used herein, the terms system, subsystem, service, programmed logic circuitry, and the like may be implemented as any suitable combination of software, hardware, firmware, and/or the like. It also will be appreciated that the storage locations herein may be any suitable combination of disk drive devices, memory locations, solid state drives, storage area network (SAN) systems, and/or any other appropriate tangible computer readable storage medium. It also will be appreciated that the techniques described herein may be accomplished by having a processor execute instructions that may be tangibly stored on a computer readable storage medium.

Various forms of computer readable media/transmissions may be involved in carrying data (e.g., sequences of instructions) to a processor. For example, data may be (i) delivered from a memory to a processor; (ii) carried over any type of transmission medium (e.g., wire, wireless, optical, etc.); (iii) formatted and/or transmitted according to numerous formats, standards or protocols, such as Ethernet (or IEEE 802.3), Bluetooth™, and TCP/IP, CDMA, 5G, etc.; and/or (iv) encrypted to ensure privacy or prevent fraud in any of a variety of ways well known in the art.

As used herein, the term "non-transitory computer-readable storage medium" includes a register, a cache memory, a ROM, a semiconductor memory device (such as a D-RAM, S-RAM, or other RAM), a magnetic medium such as a flash memory, a hard disk, a magneto-optical medium, an optical medium such as a CD-ROM, a DVD, or Blu-Ray Disc, or other type of device for non-transitory electronic data storage. The term "non-transitory computer-readable storage medium" does not include a transitory, propagating electromagnetic signal.

EXAMPLES

Example 1

In an example, an RTB device includes a minimal spanning basis set of sensor elements in combination with a tunable algorithm that may sense a wide variety of disease states. More specifically, the RTB device with 64 IDEs may have 5 total functionalization schemes (pristine, gold, silver, copper, and platinum cluster decorated). Clusters may have the approximate size of 10-30 nm in diameter. 3A molecular sieves may be located adjacent to the device and water vapor removal from a 5 mL quantity of an end tidal breath may occur within 1 minute. The cassette includes chemically resistant one way valves, packaged sensor, and desiccant. The RTB may be sampled at a 1 Hz rate while applying a constant 100 mV bias to each IDE. Data collection and analysis focuses on change in resistivity from baseline as well as kinetics of response and recovery. These metrics may be fed into PCA to determine initial clustering. Classification may initially occur with support vector machines with a kernel based on minimizing the number of samples which violate the decision boundary. Different diseases states may be classified based on changes in the algorithm. Beyond identification of the disease states, further data collection may be used to train the sensor to identify disease progression.

Example 2

Figure 17:
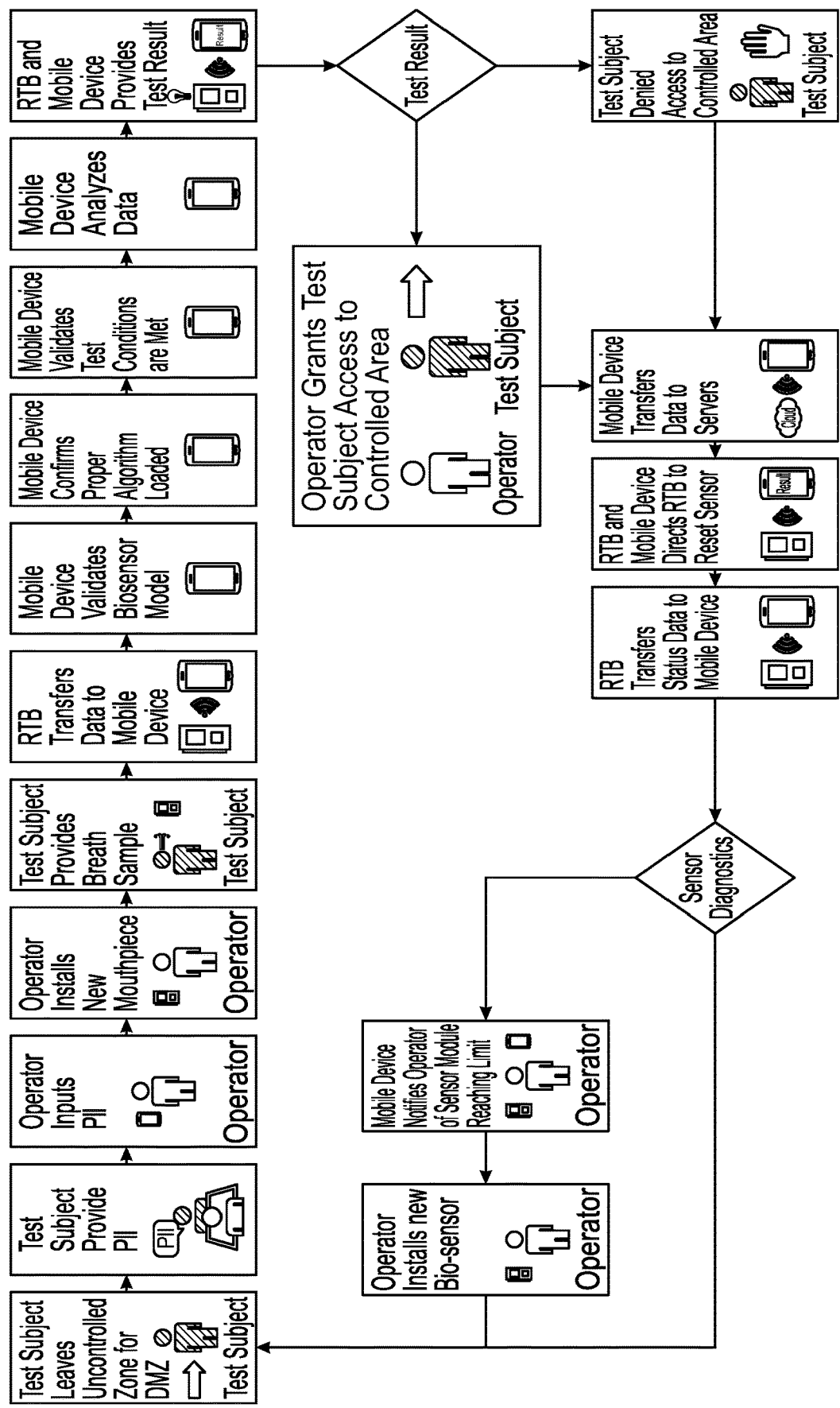
FIG. 17 illustrates a use case for deploying the RTB for testing, according to some embodiments.

An example use case, shown in FIG. 17, is as follows:

1. A Test Subject enters the DMZ from an Uncontrolled Zone and requests access to the Controlled Zone. The DMZ has a RTB, that is Bluetooth enabled, and an Operator who has a Mobile Device that is connected via Bluetooth to the RTB. The Mobile Device runs the Custom App.

2. Optionally, the Test Subject is issued a high frequency RFID SSB that has a unique ID for the RTB system assigned to it.

3. The Test Subject may elect to provide personally identifiable information (PII) at this time. PII may not be required in some embodiments. The Operator or the Test Subject may be inputting the PII into the Mobile Device. Capture of PII may create the need for a HIPAA, FedRAMP, and GDPR or other compliance security reviews where a person's personal data is handled/stored. Individual country security concerns may also need to be considered where people's information is captured.

4. The Operator replaces/sanitizes the mouthpiece on the RTB.

5. The Test Subject exhales into the mouthpiece on the RTB. Nano-sensors will check for volatile organic compounds. In an example embodiments, there is an array of 64 sensors, and a minimum of 32 is be used.

6. The Operator initiates the collection process from the RTB App.

7. The RTB then runs a test, at 5-6 sensor state captures a second. Each RTB test-run results in a file. In one example, the file is a CSV file that has a row of comma separated values for each sensor capture, where each value reflects the 32 to 64 sensors' state at the time of the capture. If the RTB runs for 30 seconds, it would produce 15-180 rows in the CSV file. One minute, 30-360 rows. In some embodiments, multiple sensor arrays can connect to a single Mobile Device. In some embodiments, a single Bluetooth RTB connected to a single Mobile Device (e.g., iOS iPhone) running the RTB application. In some embodiments, multiple sensor arrays connect to a multiple Mobile Devices of varying types, and the incoming connection may also be WiFi or other mobile communication network.

8. Once the RTB's run is complete, the test results in the file are cached on the RTB.

9. The RTB may be run multiple times and produce multiple files. At some point, the Operator will choose to download the files to the RTB Application on the Operator's Mobile Device from the RTB.

10. The RTB will log the total number of cycles the Modular Sensor has run.

11. Once the RTB's files are received, the RTB application applies a moving average algorithm to make a final determination as to what each sensor state is, and what that means, i.e. the aggregate determination is a positive or negative Screening Results for COVID-19. The code-set for the determination algorithm is preferably modular, such that the algorithm can be changed. In some example embodiments, the algorithm executes on the phone/tablet/desktop "mobile" device, not the sensor array, not the cloud. The app may be driving the session and the Bluetooth framework will manage the network protocols. The devices may also need to be securely paired (e.g. using a PIN) before a session scan be established between the RTB mobile platform and the VOC sensor array. Once the encrypted connection is established, the RTB and RTB app on the Mobile Device are "paired".

12. Once the RTB app has provided a Screening Result based on the file's data, the file and the algorithm's final determination is combined with PII and other meta-information about the test, including: SSB ID, PII, Determination Algorithm Uniquely Identifiable Version (used at point in time), GPS-based test facility location, Date, Time, Unique Identifier (such as RTB Device ID, MAC address, or some form of a Token) that uniquely identifies the RTB.

13. The RTB App then displays the determination result set and display the determination result to the Operator. Optional: The RTB App transmits Screening Result to the RTB and the RTB provides an indication of the Screening Result (e.g., by using indicator LEDs on the RTB).

14. The Operator will use the Screening Result to provide direction to the Test Subject. (e.g., a negative Screening Results indicates the Operator can grant the Test Subject access to the Controlled Zone.)

15. The RTB will reset/sanitize the sensor for the next Test Subject.

16. The Mobile Device will notify the Operator when the Modular Sensor requires replacement based on the number of cycles or sensor results indicating poor performance.

17. The Operator will remove and dispose of the installed Modular Sensor and install a new Modular Sensor. The Mobile Device will query the RTB for data and validate the results are within the expected range. The Mobile provide validation to the Operator that the Modular Sensor is communicating properly.

18. At some point, the Operator will batch upload test result sets to the cloud from the RTB Application. This means that RTB files are sent as a "package" (or FIFO) to a cloud API Service for storage (e.g., Azure), which stores the information into a database (e.g., CosmosDB).

19. Web App may demonstrate "done" by reading the test results now stored in the database. A data consumer can query result sets by an SSB for a person's most recent test result set, and where it happened (meta-information from result set).

20. At some frequency, the Operator will sanitize the external surfaces of the RTB.

Those skilled in the art will appreciate that the presently disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

Numerous examples are provided herein to enhance the understanding of the present disclosure. A specific set of statements are provided as follows.

Statement 1. A rapid breath testing system comprising: a mouthpiece operable to receive air flow from a breath; a cassette comprising a biosensor and a cassette conduit having a cassette inlet and a cassette outlet, wherein the mouthpiece is removably connected to the cassette inlet such that at least a sample of the air flow passes through the cassette conduit and over the biosensor, wherein the biosensor comprises a plurality of graphene-based sensors and the biosensor is operable to detect a presence of at least one volatile organic compound (VOC) in the air flow sample through the graphene-based sensors.

Statement 2. The rapid breath testing system of Statement 1, wherein the mouthpiece further comprises a passive check valve.

Statement 3. The rapid breath testing system of Statement 2, wherein the passive check valve is an umbrella check valve.

Statement 4. The rapid breath testing system of Statement 1, wherein the mouthpiece further comprises a body comprising a body conduit having a breath inlet, an exhaust, and a sample air flow outlet.

Statement 5. The rapid breath testing system of Statement 4, wherein 80% to 95% of the air flow from the breath entering the breath inlet exits through the exhaust and any remaining air flow is the air flow sample.

Statement 6. The rapid breath testing system of Statement 4, wherein the sample air flow outlet is operable to removably connect to the cassette inlet.

Statement 7. The rapid breath testing system of Statement 6, wherein the air flow sample exits the body conduit of the mouthpiece through the sample air flow outlet and into the cassette inlet.

Statement 8. The rapid breath testing system of Statement 4, wherein the mouthpiece further comprises a filter within the body conduit.

Statement 9. The rapid breath testing system of Statement 4, wherein the mouthpiece further comprises a desiccant.

Statement 10. The rapid breath testing system of Statement 9, wherein the mouthpiece comprises a body made of the desiccant.

Statement 11. The rapid breath testing system of Statement 1, wherein the mouthpiece is disposable.

Statement 12. The rapid breath testing system of Statement 1, wherein the cassette is reusable.

Statement 13. The rapid breath testing system of Statement 1, wherein the cassette comprises a flow path housing defining the cassette conduit, the cassette inlet, and the cassette outlet.

Statement 14. The rapid breath testing system of Statement 13, wherein the flow path housing comprises a tab extending downward from the cassette inlet.

Statement 15. The rapid breath testing system of Statement 13, wherein the cassette conduit comprises an analysis chamber having a wider diameter than a diameter of the cassette conduit before and after the analysis chamber.

Statement 16. The rapid breath testing system of Statement 15, wherein the flow path housing is open on a first end and a second end of the analysis chamber.

Statement 17. The rapid breath testing system of Statement 16, wherein the biosensor is adjacent to the first end of the analysis chamber such that it is exposed to the air flow sample flowing through the analysis chamber and forms a seal on the first end of the analysis chamber.

Statement 18. The rapid breath testing system of Statement 1, wherein the cassette further comprises a UV radiation source configured to emit UV radiation towards the biosensor to remove at least a portion of VOC bound to the biosensor.

Statement 19. The rapid breath testing system of Statement 18, wherein the cassette conduit comprises an analysis chamber with a first end and a second end and further wherein the UV radiation source is adjacent to the second end of the analysis chamber, opposite the biosensor, such that the UV radiation passes through the analysis chamber and onto at least a portion of the biosensor and forms a seal on the second end of the analysis chamber.

Statement 20. The rapid breath testing system of Statement 1, wherein the cassette further comprises a heater operable to remove the at least a portion of the VOC bound to the biosensor.

Statement 21. The rapid breath testing system of Statement 1, further comprising: an O-ring seal between the biosensor and a flow path housing defining the cassette conduit; and an O-ring between a UV radiation source and the flow path housing.

Statement 22. The rapid breath testing system of Statement 1, wherein the cassette comprises a first check valve at the cassette inlet and a second check valve at the cassette outlet.

Statement 23. The rapid breath testing system of Statement 22, wherein at least one of the first check valve, the second check valve, or a combination thereof is an umbrella check valve.

Statement 24. The rapid breath testing system of Statement 22, wherein the first check valve and the second check valve are contained within valve housings.

Statement 25. The rapid breath testing system of Statement 1, wherein the cassette inlet is located on a first edge of the cassette and the cassette outlet is located on a second edge of the cassette.

Statement 26. The rapid breath testing system of Statement 25, wherein the cassette conduit comprises at least one 90° turn.

Statement 27. The rapid breath testing system of Statement 1, wherein the biosensor includes a plurality of subsets of graphene-based sensors of the plurality of graphene-based sensors and each subset of graphene-based sensors of the plurality of subsets of graphene-based sensors is doped with a corresponding different type of metal of a plurality of different types of metal.

Statement 28. The rapid breath testing system of Statement 27, wherein the plurality of different types of metal include at least two of gold, silver, titanium, platinum, and copper.

Statement 29. The rapid breath testing system of Statement 27 wherein each subset of graphene-based sensors of the plurality of subsets of graphene-based sensors is configured to generate a different characteristic response in a physical presence of the VOC.

Statement 30. The rapid breath testing system of Statement 29, wherein each graphene-based sensor in a corresponding subset of graphene-based sensors is configured to generate a same characteristic response in the physical presence of the VOC.

Statement 31. The rapid breath testing system of Statement 29, wherein the VOC is detected based on different characteristic responses generated by the plurality of subsets of graphene-based sensors in the physical presence of the VOC.

Statement 32. The rapid breath testing system of Statement 27, wherein each subset of graphene-based sensors of the plurality of subsets of graphene-based sensors is doped with a different element.

Statement 33. The rapid breath testing system of Statement 32, wherein the different elements change a fermi level of graphene of each subset of graphene-based sensors to corresponding different changed fermi levels.

Statement 34. The rapid breath testing system of Statement 33, wherein each of the corresponding different changed fermi levels is within 2 eV of the fermi level of the graphene.

Statement 35. The rapid breath testing system of Statement 27, wherein the plurality of subsets of graphene-based sensors includes four or five different subsets of graphene-based sensors that are configured to generate a different characteristic response in a physical presence of the VOC.

Statement 36. The rapid breath testing system of Statement 35, wherein the four or five different subsets of graphene-based sensors each include four or five graphene-based sensors.

Statement 37. The rapid breath testing system of Statement 1, wherein the biosensor is coupled to a processor configured to receive a signal that is indicative of an occurrence of at least one VOC binding to the biosensor.

Statement 38. The rapid breath testing system of Statement 1, wherein the VOC is SARS-CoV-2.

Statement 39. The rapid breath testing system of Statement 1, further comprising a base operable to receive the cassette.

Statement 40. The rapid breath testing system of Statement 31, wherein the base is configured to receive the cassette in a removable manner such that when the cassette is disposed in the base, the cassette conduit is directly coupled to a sample air flow outlet of a mouth piece to form a flow path for the air flow sample that extends from the mouthpiece through the cassette and is physically isolated from all portions of the base.

Statement 41. The rapid breath testing system of Statement 31, wherein the cassette is configured to be sanitized separate from the base after one or more uses of the cassette during one or more testing phases of the rapid breath testing system while the cassette is coupled to the base and the mouthpiece.

Statement 42. The rapid breath testing system of Statement 31, wherein the base comprises a connector having a single direction track for receiving the cassette.

Statement 43. The rapid breath testing system of Statement 31, wherein the base comprises: one or more processors; and a computer-readable medium comprising instructions stored therein, which when executed by the one or more processors, cause the one or more processors to: collect data generated from the biosensor after contact with the at least one VOC; store the data in a memory; analyze the data to make a determination whether the VOC is present in the sample air flow; and facilitate transmission of a result of the determination.

Statement 44. The rapid breath testing system of Statement 43, wherein the biosensor electronically connects to the processor of the base when the cassette is physically coupled to the base.

Statement 45. The rapid breath testing system of Statement 43, wherein the instructions which when executed by the one or more processors, cause the one or more processors to transmit either or both the data and results of the determination.

Statement 46. The rapid breath testing system of Statement 45, wherein either or both the data and the results of the determination are transmitted via a wireless personal area network (PAN) to a mobile device.

Statement 47. The rapid breath testing system of Statement 43, wherein the base includes a battery configured to provide power to the biosensor when the cassette is physically coupled to the base.

Statement 48. The rapid breath testing system of Statement 1, further comprising one or more indicators that are perceivable by a user and the one or more indicators are operable to indicate to the user if a VOC is detected.

Statement 49. A mouthpiece comprising: a body; a body conduit through the body of the mouthpiece, the body conduit comprising a breath inlet, an exhaust, and a sample air flow outlet; and a check valve within the body conduit, wherein the mouthpiece is operable to receive air flow from a breath of a user at the breath inlet and pass at least a sample of the air flow out the sample air flow outlet, and wherein the check valve is operable to prevent backflow of the air flow to the user.

Statement 50. The mouthpiece of Statement 49, wherein 80% to 95% of the air flow from the breath entering the breath inlet exits through the exhaust and any remaining air flow is the air flow sample.

Statement 51. The mouthpiece of Statement 49, further comprising a filter within the body conduit.

Statement 52. The mouthpiece of Statement 49, wherein the sample air flow outlet is configured to be coupled to a cassette inlet of a cassette comprising a biosensor including a plurality of graphene-based sensors and the biosensor is operable to detect at least one volatile organic compound (VOC) through the plurality of graphene-based sensors.

Statement 53. The mouthpiece of Statement 52, wherein the check valve is operable to prevent backflow of the air flow to the user from either or both the body conduit of the mouthpiece and a cassette conduit of the cassette.

Statement 54. The mouthpiece of Statement 49, further comprising a mouthguard operable to prevent the user from overshooting the mouthpiece.

Statement 55. The mouthpiece of Statement 49, wherein the mouthpiece is disposable.

Statement 56. The mouthpiece of Statement 49, wherein the body comprises a first housing and a second housing, and wherein the first housing snap fits to the second housing to form the body.

Statement 57. A cassette comprising: a biosensor comprising a plurality of graphene-based sensors, wherein the biosensor is operable to detect a presence of at least one volatile organic compound (VOC) in an air flow sample through the plurality of graphene-based sensors; and a cassette conduit having a cassette inlet and a cassette outlet, wherein the air flow sample passes through the cassette conduit and over the biosensor and the cassette.

Statement 58. The cassette of Statement 57, wherein the cassette is reusable.

Statement 59. The cassette of Statement 57, further comprising a flow path housing defining the cassette conduit, the cassette inlet, and the cassette outlet.

Statement 60. The cassette of Statement 59, wherein the flow path housing comprises a tab extending downward from the cassette inlet.

Statement 61. The cassette of Statement 57, wherein the cassette conduit comprises an analysis chamber having a wider diameter than a diameter of the cassette conduit before and after the analysis chamber.

Statement 62. The cassette of Statement 61, further comprising a flow path housing defining the cassette conduit, the cassette inlet, and the cassette outlet and wherein the flow path housing is open on a first end and a second end of the analysis chamber.

Statement 63. The cassette of Statement 57, wherein the cassette conduit comprises a analysis chamber with a first end and a second end and the biosensor is adjacent to the first end of the analysis chamber such that it is exposed to the air flow sample flowing through the analysis chamber and forms a seal on the first end of the analysis chamber.

Statement 64. The cassette of Statement 57, wherein the cassette further comprises a UV radiation source configured to emit UV radiation towards the biosensor to remove any VOC bound to the biosensor.

Statement 65. The cassette of Statement 64, wherein the cassette conduit comprises an analysis chamber with a first end and a second end and the UV radiation source is adjacent to the second end of the analysis chamber, opposite the biosensor, such that the UV radiation passes through the analysis chamber and onto the biosensor and forms a seal on the second end of the analysis chamber.

Statement 66. The cassette of Statement 57, wherein the cassette further comprises a heater operable to remove any VOC bound to the biosensor with the UV radiation.

Statement 67. The cassette of Statement 57, further comprising: a flow path housing defining the cassette conduit, the cassette inlet, and the cassette outlet; and an O-ring seal between the biosensor and the flow path housing and an O-ring between a UV radiation source and the flow path housing.

Statement 68. The cassette of Statement 57, further comprising a check valve at the cassette inlet and at the cassette outlet.

Statement 69. The cassette of Statement 68, wherein the check valves are umbrella check valves.

Statement 70. The cassette of Statement 68, wherein the check valves are contained within a valve housing.

Statement 71. The cassette of Statement 57, wherein the cassette inlet is located on a first edge of the cassette and the cassette outlet is located on a second edge of the cassette.

Statement 72. The cassette of Statement 57, wherein the cassette conduit comprises at least one 90° turn.

Statement 73. The cassette of Statement 57, wherein the biosensor includes a plurality of subsets of graphene-based sensors of the plurality of graphene-based sensors and each subset of graphene-based sensors of the plurality of subsets of graphene-based sensors is doped with a corresponding different type of metal of a plurality of different types of metal.

Statement 74. The cassette of Statement 73, wherein the plurality of different types of metal include at least two of gold, silver, titanium, platinum, and copper.

Statement 75. The cassette of Statement 73, wherein each subset of graphene-based sensors of the plurality of subsets of graphene-based sensors is configured to generate a different characteristic response in a physical presence of the VOC.

Statement 76. The cassette of Statement 75, wherein each graphene-based sensor in a corresponding subset of graphene-based sensors is configured to generate a same characteristic response in the physical presence of the VOC.

Statement 77. The cassette of Statement 75, wherein the VOC is detected based on different characteristic responses generated by the plurality of subsets of graphene-based sensors in the physical presence of the VOC.

Statement 78. The cassette of Statement 73, wherein each subset of graphene-based sensors of the plurality of subsets of graphene-based sensors is doped with a different element.

Statement 79. The cassette of Statement 78, wherein the different elements change a fermi level of graphene of each subset of graphene-based sensors to corresponding different changed fermi levels.

Statement 80. The cassette of Statement 79, wherein each of the corresponding different changed fermi levels is within 2 eV of the fermi level of the graphene.

Statement 81. The cassette of Statement 73, wherein the plurality of subsets of graphene-based sensors includes four or five different subsets of graphene-based sensors that are configured to generate a different characteristic response in a physical presence of the VOC.

Statement 82. The cassette of Statement 81, wherein the four or five different subsets of graphene-based sensors each include four or five graphene-based sensors.

Statement 83. The cassette of Statement 57, wherein the biosensor comprises a processor configured to receive a signal that is indicative of an occurrence of at least one VOC binding to the biosensor.

Statement 84. The cassette of Statement 83, wherein the VOC is SARS-CoV-2.

Statement 85. A method for detecting at least one volatile organic compound (VOC) in an air flow sample, the method comprising: receiving an air flow from a breath passed into a breath inlet of a mouthpiece of a rapid breath testing system, the rapid breath testing system further comprising a cassette comprising a biosensor connected to the mouthpiece, wherein a sample of the air flow passes from a sample air flow outlet of the mouthpiece through a cassette conduit of the cassette; detecting, through a plurality of graphene-based sensors of the biosensor, at least one volatile organic compound (VOC) in the air flow sample.

Statement 86. The method of Statement 85, wherein 80% to 95% of the air flow from the breath entering the breath inlet exits through an exhaust of the mouthpiece and any remaining air flow is the air flow sample.

Statement 87. The method of Statement 85, wherein the mouthpiece further comprises a check valve to prevent backflow of the air flow.

Statement 88. The method of Statement 85, further comprising connecting the mouthpiece to the cassette prior to receiving the air flow.

Statement 89. The method of Statement 85, further comprising connecting the cassette to a base that is configured to receive the cassette in a removable manner.

Statement 90. The method of Statement 89, further comprising sending data from the biosensor after contact with the at least one VOC to a processor in the base.

Statement 91. The method of Statement 90, further comprising storing and analyzing the data to determine a presence of the at least one VOC in the sample air flow.

Statement 92. The method of Statement 90, further comprising providing an indicator on the base if the at least one VOC is detected.

Statement 93. The method of Statement 90, further comprising transmitting either or both the data and a result of a determination of a presence of the at least on VOC in the sample air flow to a mobile device.

Statement 94. The method of Statement 90, further comprising resetting the biosensor after receiving the sample air flow.

Statement 95. The method of Statement 94, wherein resetting the biosensor comprises transmitting UV light onto at least a portion of the biosensor to release any bound VOC from the biosensor.

Statement 96. The method of Statement 95, further comprising applying heat to at least a portion of the biosensor while transmitting the UV light.

Statement 97. The method of Statement 85, further comprising replacing the mouthpiece with a second mouthpiece.

Statement 98. The method of Statement 85, wherein the at least one VOC is SARS-CoV-2.

Statement 99. A biosensor comprising: a biosensor inlet configured to receive a sample of air flow from a breath; a plurality of subsets of graphene-based sensors of a plurality of graphene-based sensors that are each configured to: encounter corresponding portions of the air flow sample received at the biosensor inlet; and facilitate detection of a volatile organic compound (VOC) in the air flow sample based on encounters of the corresponding portions of the air flow sample with each of the plurality of subsets of graphene-based sensors.

Statement 100. The biosensor of Statement 99, wherein each subset of graphene-based sensors of the plurality of subsets of graphene-based sensors is configured to generate a different characteristic response in a physical presence of the VOC.

Statement 101. The biosensor of Statement 100, wherein each graphene-based sensor in a corresponding subset of graphene-based sensors is configured to generate a same characteristic response in the physical presence of the VOC.

Statement 102. The biosensor of Statement 100, wherein the VOC is detected based on different characteristic responses generated by the plurality of subsets of graphene-based sensors in the physical presence of the VOC.

Statement 103. The biosensor of Statement 99, wherein each subset of graphene-based sensors of the plurality of subsets of graphene-based sensors is doped with a corresponding different type of metal of a plurality of different types of metal.

Statement 104. The biosensor of Statement 103, wherein the plurality of different types of metal include at least two of gold, silver, titanium, platinum, and copper.

Statement 105. The biosensor of Statement 99, each subset of graphene-based sensors of the plurality of subsets of graphene-based sensors is doped with a different element.

Statement 106. The biosensor of Statement 105, wherein the different elements change a fermi level of graphene of each subset of graphene-based sensors to corresponding different changed fermi levels.

Statement 107. The biosensor of Statement 106, wherein each of the corresponding different changed fermi levels is within 2 eV of the fermi level of the graphene.

Statement 108. The biosensor of Statement 99, wherein the plurality of subsets of graphene-based sensors includes four or five different subsets of graphene-based sensors that are configured to generate a different characteristic response in a physical presence of the VOC.

Statement 109. The biosensor of Statement 108, wherein the four or five different subsets of graphene-based sensors each include four or five graphene-based sensors.

What is claimed is:

1. A rapid breath testing system comprising:
a mouthpiece operable to receive air flow from a breath; and
a cassette comprising a biosensor and a cassette conduit having a cassette inlet and a cassette outlet, wherein the mouthpiece is removably connected to the cassette inlet such that at least a sample of the air flow passes through the cassette conduit and over the biosensor,
wherein the biosensor comprises a plurality of graphene-based sensors and the biosensor is operable to detect a presence of at least one volatile organic compound (VOC) comprising a marker for a disease in the air flow sample through the plurality of graphene-based sensors, and wherein the disease is COVID-19.

2. The rapid breath testing system of claim 1, wherein the mouthpiece further comprises a passive check valve.

3. The rapid breath testing system of claim 2, wherein the passive check valve is an umbrella check valve.

4. The rapid breath testing system of claim 1, wherein the mouthpiece further comprises a body comprising a body conduit having a breath inlet, an exhaust, and a sample air flow outlet.

5. The rapid breath testing system of claim 4, wherein 80% to 95% of the air flow from the breath entering the breath inlet exits through the exhaust and any remaining air flow is the air flow sample.

6. The rapid breath testing system of claim 4, wherein the mouthpiece further comprises a desiccant.

7. The rapid breath testing system of claim 1, wherein the mouthpiece is disposable and the cassette is reusable.

8. The rapid breath testing system of claim 1, wherein the cassette comprises a flow path housing defining the cassette conduit, the cassette inlet, and the cassette outlet.

9. The rapid breath testing system of claim 8, wherein the cassette conduit comprises an analysis chamber having a wider diameter than a diameter of the cassette conduit before and after the analysis chamber.

10. The rapid breath testing system of claim 9, wherein the flow path housing is open on a first end and a second end of the analysis chamber.

11. The rapid breath testing system of claim 10, wherein the biosensor is adjacent to the first end of the analysis chamber such that it is exposed to the air flow sample flowing through the analysis chamber and forms a seal on the first end of the analysis chamber.

12. The rapid breath testing system of claim 1, wherein the cassette further comprises a UV radiation source configured to emit UV radiation towards the biosensor to remove at least a portion of VOC bound to the biosensor.

13. The rapid breath testing system of claim 1, wherein the cassette further comprises a heater operable to remove the at least a portion of the VOC bound to the biosensor.

14. The rapid breath testing system of claim 1, wherein the cassette comprises a first check valve at the cassette inlet and a second check valve at the cassette outlet.

15. The rapid breath testing system of claim 14, wherein at least one of the first check valve, the second check valve, or a combination thereof is an umbrella check valve.

16. The rapid breath testing system of claim 1, wherein the biosensor includes a plurality of subsets of graphene-based sensors of the plurality of graphene-based sensors and each subset of graphene-based sensors of the plurality of subsets of graphene-based sensors is doped with a corresponding different type of metal of a plurality of different types of metal.

17. The rapid breath testing system of claim 16, wherein the plurality of different types of metal include at least two of gold, silver, titanium, platinum, and copper.

18. The rapid breath testing system of claim 16, wherein each subset of graphene-based sensors of the plurality of subsets of graphene-based sensors is doped with a different element.

19. The rapid breath testing system of claim 18, wherein the different elements change a fermi level of graphene of each subset of graphene-based sensors to corresponding different changed fermi levels.

20. The rapid breath testing system of claim 19, wherein each of the corresponding different changed fermi levels is within 2 eV of the fermi level of the graphene.

21. The rapid breath testing system of claim 16, wherein the plurality of subsets of graphene-based sensors includes four or five different subsets of graphene-based sensors that are configured to generate a different characteristic response in a physical presence of the VOC.

22. The rapid breath testing system of claim 21, wherein the four or five different subsets of graphene-based sensors each include four or five graphene-based sensors.

23. The rapid breath testing system of claim 1, wherein the biosensor is coupled to a processor configured to receive a signal that is indicative of an occurrence of at least one VOC binding to the biosensor.

24. The rapid breath testing system of claim 1, further comprising a base operable to receive the cassette.

25. The rapid breath testing system of claim 24, wherein the base is configured to receive the cassette in a removable manner such that when the cassette is disposed in the base, the cassette conduit is directly coupled to a sample air flow outlet of the mouthpiece to form a flow path for the air flow sample that extends from the mouthpiece through the cassette and is physically isolated from all portions of the base.

26. The rapid breath testing system of claim 24, wherein the base comprises:
  one or more processors; and
  a computer-readable medium comprising instructions stored therein, which when executed by the one or more processors, cause the one or more processors to:
   collect data generated from the biosensor after contact with the at least one VOC;
  store the data in a memory;
   analyze the data to make a determination whether the VOC is present in the sample air flow; and
   facilitate transmission of a result of the determination.

27. The rapid breath testing system of claim 26, wherein the biosensor electronically connects to the processor of the base when the cassette is physically coupled to the base.

28. The rapid breath testing system of claim 26, wherein the instructions which when executed by the one or more processors, cause the one or more processors to transmit either or both the data and results of the determination.

29. The rapid breath testing system of claim 1, further comprising one or more indicators that are perceivable by a user and the one or more indicators are operable to indicate to the user if a VOC is detected.

* * * * *